United States Patent [19]
Hirata

[11] Patent Number: 6,040,291
[45] Date of Patent: Mar. 21, 2000

[54] ANTIMICROBIAL PEPTIDE

[75] Inventor: Michimasa Hirata, Morioka, Japan

[73] Assignee: Seikagaku Corporation, Tokyo, Japan

[21] Appl. No.: 09/276,202

[22] Filed: Mar. 25, 1999

[30] Foreign Application Priority Data

Mar. 25, 1998 [JP] Japan .................................. 10-078136
Jun. 23, 1998 [JP] Japan .................................. 10-176466

[51] Int. Cl.$^7$ .......................... A61K 38/10; A61K 38/16;
B01D 15/00; C07K 7/08; C07K 14/00
[52] U.S. Cl. ........................... 514/12; 210/690; 210/908;
514/13; 525/54.1; 530/324; 530/326; 530/810;
536/127
[58] Field of Search .................... 530/324, 325,
530/326, 810, 811, 812, 813, 814, 815,
816, 817; 514/12, 13; 525/54.1; 210/679,
690, 691, 692, 906, 908, 17.9, 18.2, 18.5,
117, 127

[56] References Cited

U.S. PATENT DOCUMENTS

| | | | |
|---|---|---|---|
| 5,489,676 | 2/1996 | Elshach et al. | 536/22.1 |
| 5,618,675 | 4/1997 | Larrick et al. | 435/7.1 |
| 5,633,229 | 5/1997 | Nokryakov et al. | 514/12 |
| 5,731,415 | 3/1998 | Gazzano-Santoro et al. | 530/350 |
| 5,804,553 | 9/1998 | Kokryakov et al. | 514/151 |

FOREIGN PATENT DOCUMENTS

WO 94/02589  2/1994  WIPO .

OTHER PUBLICATIONS

Endotoxin Edited by Herman Friedman, T.W. Klein, et al., (Plenum Publishing Corporation, 1990) Investigation of Endotoxin Binding Cationic Proteins From Granulocytes; Aggluctination Of Erythrocytes Sensitized with Re–LPS, pp. 287–299.

M. Hirata, et al., Investigation of Endotoxin Binding Cationic Proteins from Granulocytes; Agglutination of Erythrocytes Sensitized with Re–LPS, Adv. Exp. Med. Biol. vol. 256, pp. 287–299(1990).

James W. Larrick, et al., Complementary DNA Sequence of Rabbit CAP18–A Unique Lipopolysaccharide Binding Protein, Biochemical and Biophysical Research Communications Vol. 179, pp. 170–175, Aug. 30, 1991.

Michimasa Hirata, et al., Unique Endotoxin–Neutralizing Proteins: Inhibition of Endotoxin–Induced Tissue Factor Generation, pp. 153–162, 1993.

Michimasa Hirata, et al., Endotoxin–Binding Synthetic Peptides With Endotoxin–Neutralizing, Antibacterial And Anticoagulant Activities, Bacterial Endotoxins: Basic to Anti–Sepsis Strategies, pp. 147–157, 1994.

Michimasa Hirata, et al., Characterization of a Rabbit Cationic Protein (CAP18) with Lipopolysaccharide–Inhibitory Activity, Infection and Immunity Apr. 1994, pp1421–1426.

(List continued on next page.)

*Primary Examiner*—Jeffrey E. Russel
*Attorney, Agent, or Firm*—Knobbe, Martens, Olson & Bear, LLP

[57] ABSTRACT

A peptide comprising at least the following amino acid sequence:
Lys Xa1 Phe Lys Arg Ile Val Xa2 Arg Ile Xaa Xa2 Phe Leu Arg Xa2 Leu Val (SEQ ID NO: 1)
wherein, Xa1 represents a hydrophobic amino acid residue, each of Xa2 independently represents a hydrophilic amino acid residue, and Xaa represents an arbitrary amino acid residue;

an antimicrobial agent, a medicine including a bacterial infection-treating agent and an endotoxin shock suppressant which each comprise the peptide as an active ingredient; and an endotoxin-removing agent comprising the peptide immobilized to an insoluble carrier.

16 Claims, 6 Drawing Sheets

OTHER PUBLICATIONS

M. Hirata, et al., Structure and Functions of Endotoxin–Binding Peptides Derived from CAP18, Bacterial Endotoxins Lipopolysaccharides From Genes to Therapy, pp. 317–326, 1995.

James W. Larrick, et al., Human CAP18: a Novel Antimicrobial Lipopolysaccharide–Binding Protein, Infection and Immunity, Apr. 1995, pp 1291–1297.

Chinpan Chen, et al., The solution structure of the active domain of CAP18—a lipopolysaccharide binding protein from rabbit leukocytes, FEBS Letters 370 (1995) pp. 45–52.

Jack B. Cowland, et al., hCap–18, a cathelin/pro–bactenecin–like protein of human neutrophil specific granules, FEBS Letters 368 (1995) pp. 173–176.

Kazuo Okada, et al., Shock, From Molecular and Cellular Level to Whole Body, Proceedings of the Third International Shock Congress—Shock '95, Hamamatsu, Japan, Oct. 21–23, 1995, 1996 Elsevier Science B. V. pp. 109–115.

Michimasa Hirata, et al., Gendai Iryo (Current Medical Treatment) Vol. 28 (special number III), pp. 2367–2375 (1996).

James W. Larrick, et al., Structural, functional analysis and localization of the human CAP18 gene, FEBS Letters 398 (1996) pp. 74–80.

Ole Sørensen, et al., An Elisa for hCAP—18, the cathelicidin present in human neutrophils and plasma, Journal of Immunological Methods 206 (1997) pp. 53–59.

Ole Sørensen, et al. The Human Antibacterial Cathelicidin, hCAP—, Is Synthesized in Myelocytes and Metamyelocytes and Localized to Specific Granules in Neutrophils, Blood, vol. 90 No. 7 (Oct. 1), 1997: pp. 2796–2803.

Michimasa Hirata, et al. Minophagen Medical Review, vol. 43, No. 1, Jan. 1998, pp. 1–15.

Teruo Kirikae, et al. Protective Effects of a Human 18–Kilodalton Cationic Antimicrobial Protein (CAP18)–Derived Peptide against Murine Endotoxemia, Infection and Immunity, May 1998, pp. 1861–1868.

A1 (27-MER; UNSUBSTITUTED)

(b) (27-MER; SUBSTITUTED)

ANTIMICROBIAL PEPTIDE

This application claims priority under 37 U.S.C. §119 of Japanese Application No. JP 10-78136, filed Mar. 25, 1998 and Japanese Application No. JP 10-176466, filed Jun. 23, 1998.

BACKGROUND OF THE INVENTION

The present invention relates to a novel antimicrobial peptide and more particularly to an antimicrobial peptide which is a partial peptide of a human-derived antimicrobial protein, in which amino acid residues thereof are partially substituted. Also, the present invention relates to an antimicrobial agent as well as a medicine such as a bacterial infection-treating agent and an endotoxin shock suppressant, each comprising the antimicrobial peptide as an active ingredient. Further, the present invention relates to an endotoxin-removing agent comprising the antimicrobial peptide immobilized on an insoluble carrier.

CAP18 (Cationic antimicrobial protein of 18 kDa) is an antimicrobial protein found in human and rabbit granulocytes.

Japanese Patent Application Laid-open No. 8-504085 (1996) describes the whole amino acid sequence of human-derived CAP18 inclusive of its signal peptide portion. Also, it describes a partial peptide comprising C-terminal 37 amino acid residues of the human-derived CAP18 having an amino acid sequence in which a sequence derived from a rabbit is substituted for a portion thereof.

MINOPHAGEN MEDICAL REVIEW, Vol. 43, No. 1, pp. 1–15 (1998) describes the whole amino acid sequence of human-derived CAP18. It also describes partial peptides comprising C-terminal 34, 32, 30, 27, 24 and 22 amino acids residues, respectively, of the human-derived CAP18. Also, it shows data on the antimicrobial activities of these peptides on *Escherichia coli*, Salmonella, methicillin-sensitive *Staphylococcus aureus* (MSSA) and methicillin-resistant *Staphylococcus aureus* (MRSA).

GENDAI IRYO (Current Medical Treatment), vol. 28 (special number III), pp. 2367–2375 (1996) describes the whole amino acid sequence of human-derived CAP18. It also describes partial peptides comprising C-terminal 34, 30, 27, 24 and 22 amino acids residues, respectively, of the human-derived CAP18. Also, it describes data on inhibition of the lipopolysaccharide (LPS; also referred to as endotoxin) activity by these peptides.

SHOCK; From Molecular and Cellular Level to Whole Body (Proceedings of the Third International Shock Congress-Shock '95, Hamamatsu, Japan, Oct. 21–23 1995), Okada, K., Ogata, H. eds. Elsevier Science B.V., pp.109–115, (1996) describes the whole amino acid sequence of human-derived CAP18. It also describes partial peptides comprising C-terminal 34, 30, 27 and 24 amino acids residues, respectively, of the human-derived CAP18. Also, it describes data on binding activities of these peptides to LPS.

Bacterial Endotoxins; Lipopolysaccharides From Genes to Therapy. Levin, J., Alving, C. R., Munford, R. S., Redl, H. eds. Wiley-Liss, Inc., New York, pp. 317–326, (1995) describes partial peptides comprising C-terminal 37 and 32 amino acids residues, respectively, of human-derived CAP18. Also, it describes data on the influences of these peptides on production of a tissue factor by LPS, on suppression of lethality due to endotoxin shock, and on an antimicrobial activity.

However, none of the above-described publications describes or suggests those peptides with substitution of another specified amino acid residue or residues for an amino acid residue or residues at specified position or positions in the portion common to the known partial peptides of CAP18. None of them describes or suggests that such partial peptides with the substitution of the specified amino acid residue or residues have an LPS-binding activity, an antimicrobial activity, and an LPS-neutralizing activity which are remarkably higher than those of the known partial peptides.

If a peptide which is derived from human and has a high LPS-binding activity, a high antimicrobial activity and a high LPS-neutralizing activity is obtained, then there can be provided at extremely low cost an antimicrobial agent, a bacterial infection-treating agent, an endotoxin shock suppressant, and the like which are safe to humans.

The present invention has been made from the above-described viewpoints, and its object is to provide a human-derived peptide having a high LPS-binding activity, a high antimicrobial activity and a high LPS-neutralizing activity and an antimicrobial agent, a bacterial infection-treating agent, an endotoxin shock suppressant, an endotoxin-removing agent, and the like which comprise the peptide as an active ingredient.

SUMMARY OF THE INVENTION

As a result of intensive investigation by the present inventors to accomplish the above-mentioned object, it has now been found that a peptide comprising a partial peptide of a human-derived CAP18 with substitution of another specified amino acid residue or residues for an amino acid residue or residues at a specified position or positions have an LPS-binding activity, an antimicrobial activity and an LPS-neutralizing activity remarkably higher than those of the known partial peptides and that such a peptide can be utilized as an antimicrobial agent, a bacterial infection-treating agent, an endotoxin shock suppressant and an endotoxin-removing agent, and the present invention has been completed.

Thus the present invention provides a peptide comprising at least the following amino acid sequence:

Lys Xa1 Phe Lys Arg Ile Val Xa2 Arg Ile Xaa Xa2 Phe Leu Arg Xa2 Leu Val (SEQ ID NO: 1)

wherein, Xa1 represents a hydrophobic amino acid residue, each of Xa2 independently represents a hydrophilic amino acid residue, and Xaa represents an arbitrary amino acid residue (hereafter, referred to as the peptide of the present invention).

The peptide of the present invention preferably has an amino acid sequence selected from the following amino acid sequences (a) to (f):

(a)
Phe Arg Lys Ser Lys Glu Lys Ile Gly Lys Leu Phe Lys Arg Ile Val Gln Arg Ile Lys Asp Phe Leu Arg Asn Leu Val (SEQ ID NO: 2), (b)
Phe Arg Lys Ser Lys Glu Lys Ile Gly Lys Leu Phe Lys Arg Ile Val Gln Arg Ile Leu Asp Phe Leu Arg Asn Leu Val (SEQ ID NO: 3), (c)
Phe Arg Lys Ser Lys Glu Lys Ile Gly Lys Phe Phe Lys Arg Ile Val Gln Arg Ile Phe Asp Phe Leu Arg Asn Leu Val (SEQ ID NO: 4), (d)
Glu Lys Ile Gly Lys Leu Phe Lys Arg Ile Val Gln Arg Ile Leu Asp Phe Leu Arg Asn Leu Val (SEQ ID NO: 5), (e)

Lys Leu Phe Lys Arg Ile Val Gln Arg Ile Leu Asp Phe Leu Arg Asn Leu Val (SEQ ID NO: 6), and (f)

Lys Leu Phe Lys Arg Ile Val Lys Arg Ile Leu Lys Phe Leu Arg Lys Leu Val (SEQ ID NO: 7).

Further, the present invention provides an antimicrobial agent, a medicine including a bacterial infection-treating agent and an endotoxin shock suppressant, which each comprise the peptide of the present invention as an active ingredient (hereinafter, referred to as the antimicrobial agent of the present invention, the medicine of the present invention, the bacterial infection-treating agent of the present invention, and the endotoxin shock suppressant of the present invention, respectively) as well as an endotoxin-removing agent comprising the peptide of the present invention immobilized to an insoluble carrier (hereinafter, referred to as the endotoxin-removing agent of the present invention).

The antimicrobial agent of the present invention may be an antimicrobial composition comprising the peptide of the present invention and a carrier. The medicine of the present invention may be a medicinal composition comprising the peptide of the present invention and a pharmaceutically acceptable carrier. The bacterial infection-treating agent of the present invention may be a bacterial infection-treating composition comprising the peptide of the present invention and a pharmaceutically acceptable carrier. The endotoxin shock suppressant of the present invention may be an endotoxin shock-suppressing composition comprising the peptide of the present invention and a pharmaceutically acceptable carrier.

DETAILED DESCRIPTION OF THE INVENTION

Figure 1:
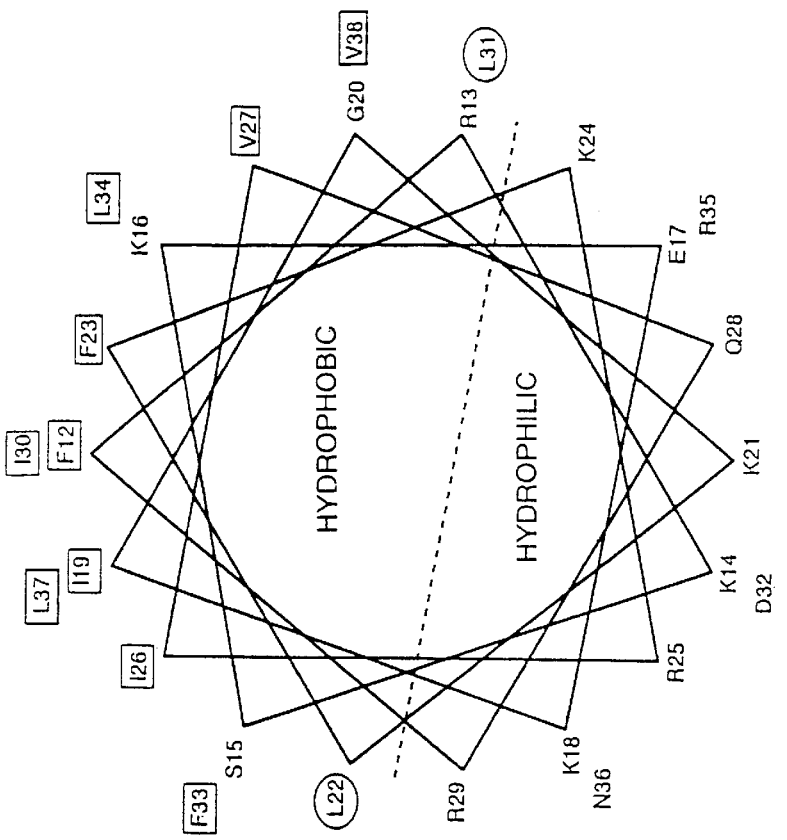
FIG. 1 is a helical wheel representation of a peptide (A1) produced in Example 1.

Hereafter, the present invention will be described in detail.

<1> Peptide of the Present Invention

The peptide of the present invention is a peptide comprising at least the following amino acid sequence:

Lys Xa1 Phe Lys Arg Ile Val Xa2 Arg Ile Xaa Xa2 Phe Leu Arg Xa2 Leu Val (SEQ ID NO: 1)

wherein, Xa1 represents a hydrophobic amino acid residue, each of Xa2 independently represents a hydrophilic amino acid residue, and Xaa represents an arbitrary amino acid residue.

The peptide of the present invention includes a peptide having any one of the following amino acid sequences (a) to (f):

(a)

Phe Arg Lys Ser Lys Glu Lys Ile Gly Lys Leu Phe Lys Arg Ile Val Gln Arg Ile Lys Asp Phe Leu Arg Asn Leu Val (SEQ ID NO: 2), (b)

Phe Arg Lys Ser Lys Glu Lys Ile Gly Lys Leu Phe Lys Arg Ile Val Gln Arg Ile Leu Asp Phe Leu Arg Asn Leu Val (SEQ ID NO: 3), (c)

Phe Arg Lys Ser Lys Glu Lys Ile Gly Lys Phe Phe Lys Arg Ile Val Gln Arg Ile Phe Asp Phe Leu Arg Asn Leu Val (SEQ ID NO: 4), (d)

Glu Lys Ile Gly Lys Leu Phe Lys Arg Ile Val Gln Arg Ile Leu Asp Phe Leu Arg Asn Leu Val (SEQ ID NO: 5), (e)

Lys Leu Phe Lys Arg Ile Val Gln Arg Ile Leu Asp Phe Leu Arg Asn Leu Val (SEQ ID NO: 6), and (f)

Lys Leu Phe Lys Arg Ile Val Lys Arg Ile Leu Lys Phe Leu Arg Lys Leu Val (SEQ ID NO: 7).

The term "amino acid" used herein means an L-amino acid unless otherwise indicated specifically.

Further, the hydrophobic amino acid residue used herein is not limited particularly so far as it is a hydrophobic amino acid residue, but is preferably a residue selected from the group consisting of glycine, alanine, valine, leucine, isoleucine, methionine, proline, phenylalanine and tryptophan. More preferred hydrophobic amino acid residue is a phenylalanine residue or a leucine residue.

In the present invention, the hydrophilic amino acid residue is not limited particularly so far as it is a hydrophilic amino acid residue but is preferably a residue selected from the group consisting of serine, threonine, cysteine, tyrosine, asparagine, glutamine, aspartic acid, glutamic acid, lysine, arginine, and histidine. A more preferred hydrophilic amino acid residue is a lysine residue.

In the present invention, the arbitrary amino acid residue means any amino acid residue selected from the above-described hydrophobic amino acid residues and hydrophilic amino acid residues. Specifically, it is preferably a residue selected from the group consisting of glycine, alanine, valine, leucine, isoleucine, methionine, proline, phenylalanine, tryptophan, serine, threonine, cysteine, tyrosine, asparagine, glutamine, aspartic acid, glutamic acid, lysine, arginine and histidine. More preferred is a hydrophobic amino acid residue, with phenylalanine or leucine being particularly preferred.

Since its amino acid sequence has been disclosed by the present invention, the peptide of the present invention can be produced by a known chemical synthesis method (see, for example, a liquid phase synthesis method, a solid phase synthesis method, etc.; Izumiya, N., Kato, T., Aoyagi, H., Waki, M., "Basis and Experiments of Peptide Synthesis", 1985, Maruzen Co., Ltd.) based on that sequence. For example, to produce a peptide having the amino acid sequence shown in SEQ ID NO: 1 by a solid phase synthesis method, if the 18-position in the amino acid sequence is a valine residue, then the peptide having the amino acid sequence shown in SEQ ID NO: 1 can be obtained by binding the carboxyl group of an α-amino group ($N^\alpha$)-protected-valine to an insoluble resin having a chloromethyl group or an oxymethyl group directly or through a spacer, removing the $N^\alpha$-protecting group, sequentially binding each protected amino acid ((N$^\alpha$)-protected and side chain functional group (if any)-protected amino acid is simply referred to as protected amino acid) in the 17-position to 1-position of the amino acid sequence by a solid phase synthesis method, and then eliminating the insoluble resin and the protecting group in the (N$^\alpha$)-group or the side chain functional group (if any) of the amino acids.

The above-described insoluble resin having a chloromethyl group or an oxymethyl group, the spacer, or the protected amino acid-bound resin which comprises an insoluble resin having a protected amino acid bound thereto according to circumstances, etc. which are used for synthesizing the peptide of the present invention, can be prepared by a known method and also there are various commercially available products.

As the insoluble resin, there can be used any resin so far as it can bind to the carboxyl group of the protected amino acid on the C-terminal directly or through spacer according to circumstances and thereafter can be eliminated. Preferred insoluble resins are, for example, chloromethyl resin (chloromethylated styrene/divinylbenzene copolymer), and an oxymethyl resin or 4-oxymethyl-Pam (phenylacetamide methyl)-resin having a spacer introduced therein in the case of a Boc (t-butyloxycarbonyl) strategy, or an oxymethylphenoxymethyl (Wang) resin and derivatives thereof in the case of an Fmoc (9-fluorenylmethyloxycarbonyl) strategy.

The protected amino acid is an amino acid whose functional group or groups is/are protected with a protecting group or groups by a known method and various protected amino acids are commercially available.

When the peptide of the present invention is synthesized, it is preferred to select any of the protecting groups shown below. First, the protecting group for the $\alpha$-amino group of an amino acid is Boc (t-butyloxycarbonyl) or Fmoc (9-fluorenylmethyloxycarbonyl). The protecting group for the guanidino group of arginine (Arg) is Tos (tosyl), NO$_2$ (nitro), Mtr (4-methoxy-2,3,6-trimethylbenzenesulfonyl) or Pmc (2,2,5,7,8-pentamethylchroman-6-sulfonyl). The protecting group for the $\epsilon$-amino group of lysine (Lys) is Z (benzyloxycarbonyl) or Cl.Z (2-cholorobenzyloxycarbonyl), Boc, or Npys (3-nitro-2-pyridinesulfenyl). The protecting group for the imidazolyl group of histidine (His) is Tos, Z, Pac (phenacyl), Bom (benzyloxymethyl), Dnp (dinitrophenyl), or Trt (trityl). The protecting group for the mercapto group of cysteine (Cys) is Bzl (benzyl), MBzl (4-methoxybenzyl), 4-MeBzl (4-methylbenzyl), Acm (acetamidomethyl), Trt, Npys, t-Bu (t-butyl), or t-BuS (t-butylthio). Preferred are MBzl, 4-MeBzl, Trt, Acm, and Npys. The protecting group for the hydroxyl group of tyrosine (Tyr) is Bzl, Cl$_2$. Bzl (2,6-dichlorobenzyl), or t-Bu or the hydroxyl group of Tyr may be non-protected. The protecting group for the indole group of tryptophan (Trp) is CHO (formyl) or the indole group of Trp may be non-protected. The protecting group for the thiomethyl group of methionine (Met) is methyl sulfoxide or the thiomethyl group of Met may be non-protected. The protecting group for the hydroxyl group of serine (Ser) and threonine (Thr) is Bzl or t-Bu. The protecting group for the carboxyl group of aspartic acid (Asp) and glutamic acid (Glu) is OBzl (benzyl ester), OtBu (t-butyl ester), OcHex (cyclohexyl ester), OPac (phenacyl ester), etc. The protecting group for the carbamide group of asparagine (Asn) and glutamine (Gln) is Trt or Xan (xanthyl).

It is preferred that each protective group be selected appropriately from those known per se depending on the conditions of peptide synthesis.

The binding of the protected amino acid is achieved by usual condensation methods, for example, a DCC (dicyclohexylcarbodiimide) method, a DIPCDI (diisopropylcarbodiimide) method (Tartar, A., et al.; J. Org. Chem., 44, 5000 (1979)), an activated ester method, a mixed or symmetric acid anhydride method, a carbonyldiimidazole method, a DCC-HONSu (N-hydroxysuccinimide) method (Weygand, F., et al., Z. Naturforsch., B, 21, 426 (1966)), a DCC-HOBt (1-hydroxybenzotriazole) method (Koenig, W., et al.; Chem. Ber., 103, 788, 2024, 2034 (1970)), a diphenylphosphorylazide method, a BOP-HOBt method (Hudson, D., J. Org. Chem., 53, 617 (1988)) using a BOP reagent (benzotriazolyl-N-hydroxytrisdimethylaminophosphonium hexafluorophosphide), a HBTU (2-(1H-benzotriazol-1-yl)-1,1,3,3-tetramethyluronium hexafluorophosphate)-HOBt method (Knorr, R., et al., Tetrahedron Lett., 30, 1927 (1989)), a TBTU (2-(1H-benzotriazol-1-yl)-1,1,3,3-tetramethyluronium tetrafluoroborate)-HOBt method (Knorr, R., et al., Tetrahedron Lett., 30, 1927 (1989)), etc. However, among these methods, preferred are the DCC method, the DCC-HOBt method, the BOP-HOBt method, the HBTU-HOBt method, and the symmetric acid anhydride method.

The condensation reaction is usually carried out in an organic solvent such as dichloromethane, dimethylformamide (DMF), N-methylpyrrolidone (NMP) and the like or a mixed solvent composed of them.

As the eliminating reagent for the protective group of $\alpha$-amino group, there can be used trifluoroacetic acid/dichloromethane, HCl/dioxane, piperidine/DMF or piperidine/NMP, etc. and these are selected appropriately depending on the kind of the protecting group.

The degree of progress of condensation reaction in each stage of synthesis can be examined by the method of E. Kaiser, et al. [Anal. Biochem., 34, 595 (1970)] (ninhydrin reaction).

As described above, a protected peptide resin having a desired amino acid sequence can be obtained.

Treatment of the protected peptide resin with hydrogen fluoride, TFMSA (trifluoromethanesulfonic acid) [E. Gross ed., Yajima, H., et al.; "The Peptide" 5, 65 (1983), Academic Press], TMSOTf (trimethylsilyl triflate [Fujii, N., et al.; J. Chem. Soc., Chem. Commun., 274 (1987)], TMSBr (trimethylsilylbromide [Fujii, N., et al.; Chem. Pharm. Bull., 35, 3880 (1987)], trifluoroacetic acid, or the like can eliminate the resin and protecting group simultaneously. The above-described eliminating reagent is selected appropriately depending on the strategy used (Boc or Fmoc) and the kinds of the resin and the protecting group. The peptide of the present invention can be produced by a series of the methods described above.

Alternatively, the peptide of the present invention can be produced by producing a polynucleotide (DNA or RNA) which corresponds to the amino acid sequence of the peptide of the present invention and producing a peptide by a genetic engineering technique using the polynucleotide.

The peptide of the present invention thus produced can be purified by isolation/purification methods for proteins generally known in the field of protein chemistry. More particularly, there can be mentioned, for example, extraction, recrystallization, salting out with ammonium sulfate, sodium sulfate, etc., centrifugation, dialysis, ultrafiltration, adsorption chromatography, ion exchange chromatography, hydrophobic chromatography, normal phase chromatography, reversed-phase chromatography, gel filtration method, gel permeation chromatography, affinity chromatography, electrophoresis, countercurrent distribution, etc. and combinations of these. Most effective is a method by reversed-phase high performance liquid chromatography.

The peptide of the present invention which is produced can be hydrolyzed with an acid, for example, hydrochloric acid, methanesulfonic acid or the like and its amino acid composition can be examined by a known method. By this, it can be presumed whether or not the peptide of the present invention is produced correctly.

More strictly, the amino acid sequence of the produced peptide is determined by a known amino acid sequence determination method (for example, Edman degradation technique, etc.) to confirm whether the peptide of the present invention is produced correctly.

The peptide of the present invention includes a form of a salt thereof. As described later on, the peptide of the present invention is particularly useful as a medicine and hence the salt of the peptide is preferably a pharmaceutically acceptable salt.

The peptide of the present invention may form a salt by addition of an acid. Examples of the acid include inorganic acids (such as hydrochloric acid, hydrobromic acid, phosphoric acid, nitric acid, and sulfuric acid) or organic carboxylic acids (such as acetic acid, propionic acid, maleic acid, succinic acid, malic acid, citric acid, tartaric acid, and salicylic acid ), acidic sugars such as glucuronic acid, galacturonic acid, gluconic acid, ascorbic acid, etc., acidic polysaccharides such as hyaluronic acid, chondroitin sulfates, alginic acid, or organic sulfonic acids (such as methanesulfonic acid, and p-toluenesulfonic acid), and the like. Of these salts, preferred is a pharmaceutically acceptable salt.

The peptide of the present invention may form a salt with a basic substance. Examples of the salt include, for example, pharmaceutically acceptable salts selected from salts with inorganic bases such as alkali metal salts (sodium salt, lithium salt, potassium salt, etc.), alkaline earth metal salts, ammonium salts, and the like or salts with organic bases, such as diethanolamine salts, cyclohexylamine salts, and the like.

Since the peptide of the present invention exhibits a high antimicrobial activity, a high endotoxin-binding activity and a high endotoxin-neutralizing activity as is apparent from the Examples described later on, the peptide of the present invention can be used as an active ingredient of the antimicrobial agent of the present invention, the bacterial infection-treating agent of the present invention, the endotoxin shock suppressant of the present invention, and the endotoxin-removing agent of the present invention as described below in detail.

The reason why the peptide of the present invention has the high antimicrobial activity, the high endotoxin (LPS)-binding activity and the high endotoxin (LPS)-neutralizing activity is presumed as follows.

Figure 2:
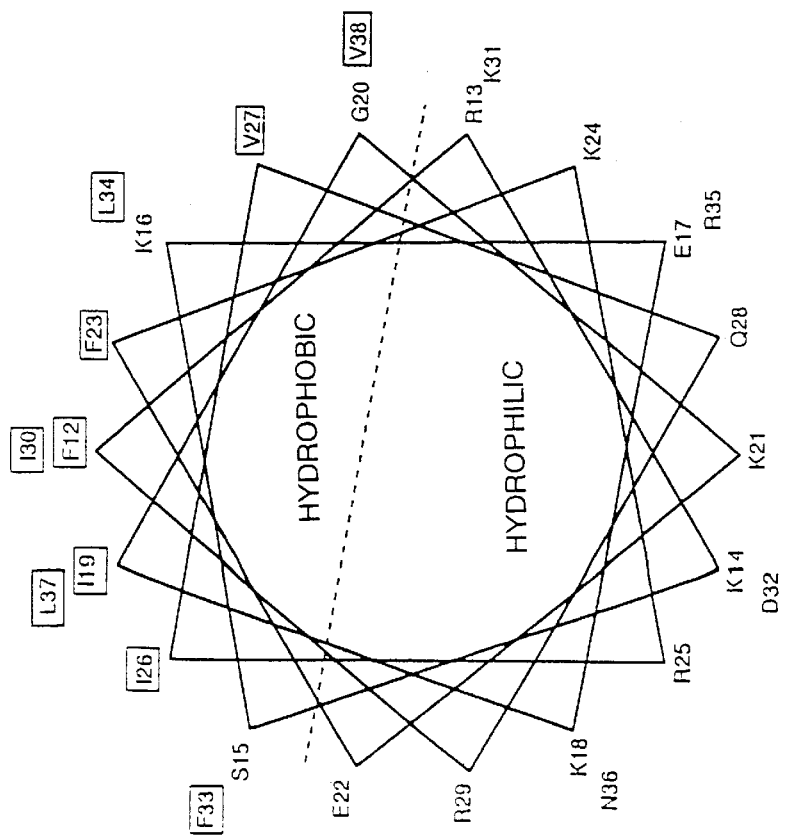
FIG. 2 is a helical wheel representation of a peptide ((b)) produced in Example 1.
Figure 3:
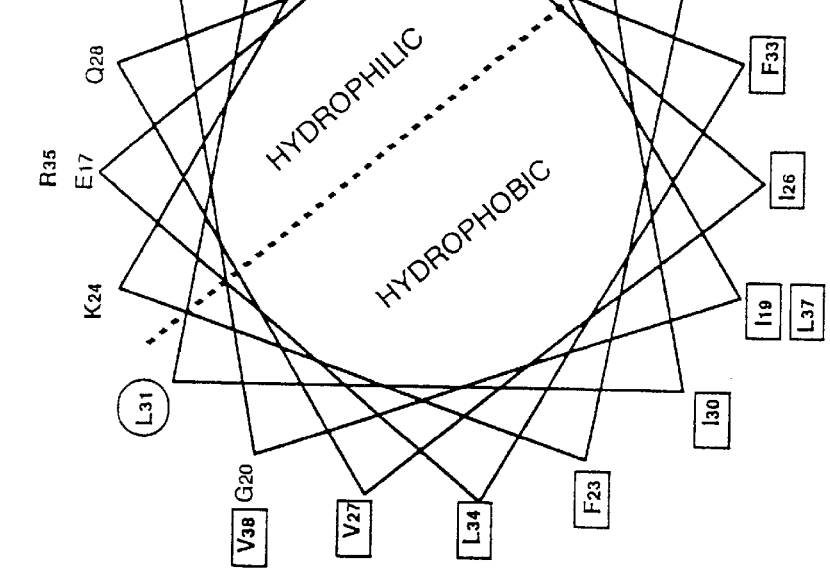
FIG. 3 is a helical wheel representation of a peptide (A3) produced in Example 1.

The peptide in the LPS-binding domain of human-derived CAP18 has an α-helix structure, which, when projected in its axial direction (helical wheel representations are shown in FIGS. 1 and 3), is observed to include a hydrophilic portion (i.e., a portion which is rich in a hydrophilic amino acid residue (basic amino acid residue) such as arginine and lysine) and a hydrophobic portion (i.e., a portion which is rich in a hydrophobic amino acid residue such as phenylalanine, leucine and isoleucine). It would be considered that the hydrophilic portion of the peptide binds ionically to a portion of the phosphate group of the lipid A portion of LPS, and the hydrophobic portion of the peptide hydrophobically binds to the fatty acid portion of the lipid A, resulting in exhibition of the antimicrobial activity and the LPS-neutralizing activity. Substitution of another specified amino acid residue for an amino acid residue at a specified position would alter the balance between the hydrophilic portion and the hydrophobic portion (FIGS. 2 and 4) and this change would be associated with an increase in the antimicrobial activity, the LPS-binding activity and LPS-neutralizing activity.

Figure 4:
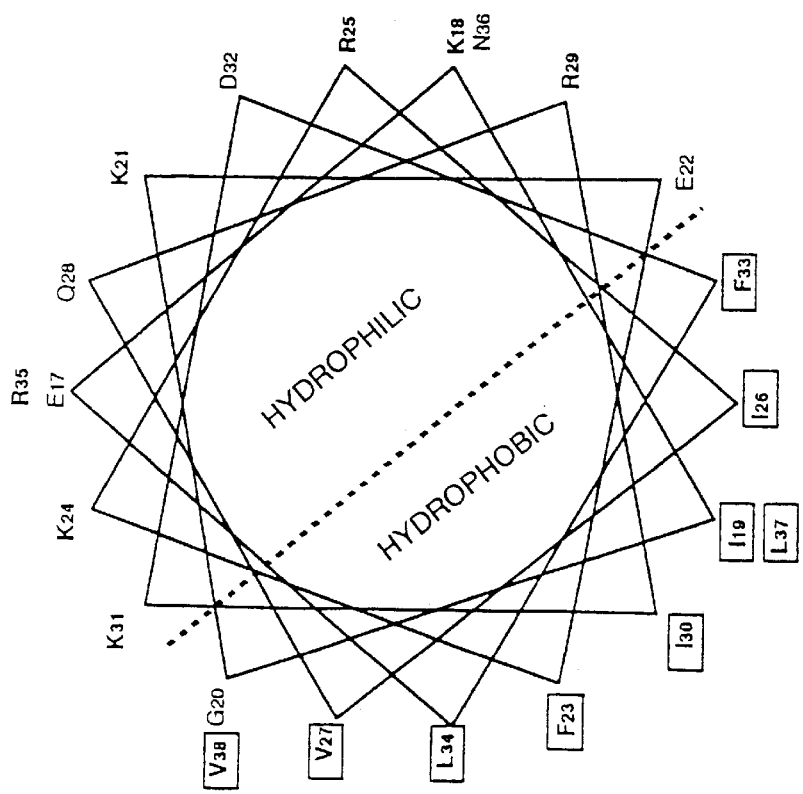
FIG. 4 is a helical wheel representation of a peptide ((d)) produced in Example 1.

The peptide of the present invention has been provided based on a basic concept that designing the amino acid sequence of the peptide by taking into consideration of the balance between the hydrophilic portion and the hydrophobic portion in the helical wheel when the α-helix structure of the peptide is projected in its axial direction, will increase the antimicrobial activity, the LPS-binding activity, and the LPS-neutralizing activity. Thus, the balance between the hydrophilic portion and the hydrophobic portion is considered to be important for the antimicrobial activity, the LPS-binding activity, and the LPS-neutralizing activity of the peptide of the present invention, and hence the peptide of the present invention also includes those peptides of which hydrophilic portion and hydrophobic portion in the helical wheel have a balance as shown in FIG. 2 or FIG. 4 (for example, those peptides with an amino acid sequence in the reverse order to the amino acid sequence of the peptide of the present invention, peptides containing D-amino acids, and peptides containing amino acids which usually do not constitute a protein (e.g., β-alanine, γ-aminobutyric acid, homocysteine, ornithine, 5-hydroxytryptophan, 3,4-dihydroxyphenylalanine, triiodothyronine, thyroxine, etc.)).

Also, the peptide of the present invention includes those peptides obtained by modifying the peptide of the present invention. Examples of the peptides includes peptides whose α-amino group or α-carboxyl group is modified, and peptides which have modified side chain functional groups. Preferred is a peptide obtainable by acetylation of the N-terminal and amidation of the C-terminal of the peptide of the present invention.

<2> Antimicrobial Agent of the Present Invention

The antimicrobial agent of the present invention is an antimicrobial agent which comprises the peptide of the present invention as an active ingredient.

The antimicrobial agent of the present invention has a potent antimicrobial activity on various gram-positive and gram-negative bacteria.

It is sufficient for the antimicrobial agent of the present invention to comprise at least the peptide of the present invention. For example, the antimicrobial agent of the present invention may consist of the peptide of the present invention alone or may be in the form of a composition comprising the peptide of the present invention and an appropriate carrier.

The antimicrobial agent of the present invention can be used as an medicine and can be used instead of or in combination with a conventional antimicrobial agent such that it is added to foods for the prevention of the foods from bacterial contamination or for preservation.

Also, the antimicrobial agent of the present invention can be applied to a surface of a suitable material or mixed with a suitable material to produce an antimicrobial material. Such an antimicrobial material can be used in the various forms of a bead, a film, a plate, a monofilament, an unwoven fabric, sponge, cloth, a knitted fabric, a short fiber, a tube, a hollow fiber, or the like. More particularly, it can be used for an artificial organ, a catheter, a suture (joining fiber) for surgical operation, a dialysis membrane, and the like as well as sanitary goods, an antimicrobial filter, and the like.

Among the peptides of the present invention used in the antimicrobial agent of the present invention, the peptide having any one of the following amino acid sequences (a) to (f) has a high antimicrobial activity as is apparent from the Examples described below in which its antimicrobial activity isF shown specifically and thus is preferred.

(a)
Phe Arg Lys Ser Lys Glu Lys Ile Gly Lys Leu Phe Lys Arg Ile Val Gln Arg Ile Lys Asp Phe Leu Arg Asn Leu Val (SEQ ID NO: 2), (b)
Phe Arg Lys Ser Lys Glu Lys Ile Gly Lys Leu Phe Lys Arg Ile Val Gln Arg Ile Leu Asp Phe Leu Arg Asn Leu Val (SEQ ID NO: 3), (c)
Phe Arg Lys Ser Lys Glu Lys Ile Gly Lys Phe Phe Lys Arg Ile Val Gln Arg Ile Phe Asp Phe Leu Arg Asn Leu Val (SEQ ID NO: 4), (d)
Glu Lys Ile Gly Lys Leu Phe Lys Arg Ile Val Gln Arg Ile Leu Asp Phe Leu Arg Asn Leu Val (SEQ ID NO: 5), (e)
Lys Leu Phe Lys Arg Ile Val Gln Arg Ile Leu Asp Phe Leu Arg Asn Leu Val (SEQ ID NO: 6), and (f)
Lys Leu Phe Lys Arg Ile Val Lys Arg Ile Leu Lys Phe Leu Arg Lys Leu Val (SEQ ID NO: 7).

Also, among the peptides having the amino acid sequences (a) to (f), the peptide having the amino acid sequence (e) or (f) exhibits a very high antimicrobial activity on both gram-negative and gram-positive bacteria and thus is particularly preferred.

<3> Medicine of the Present Invention

The medicine of the present invention is a medicine which comprises the peptide of the present invention.

The medicine of the present invention can be used for various medical applications based on the activities of the peptide of the present invention such as a high antimicrobial activity, a high endotoxin-binding activity and a high endotoxin-neutralizing activity.

It is sufficient for the medicine of the present invention to comprise at least the peptide of the present invention as an active ingredient. For example, the medicine of the present invention may consist of the peptide of the present invention alone or may be in the form of a composition comprising the peptide of the present invention and a pharmaceutically acceptable carrier. The pharmaceutically acceptable carrier which can be used in the present invention is not limited particularly and includes an excipient, a binder, a lubricant, a colorant, a disintegrant, a buffer, an isotonic agent, a preservative, an anesthetic, and the like which can be used in a medical field.

The medicine of the present invention can be applied by any suitable administration method depending on the purpose of treatment and selected from injection (subcutaneous, intracutaneous, intravenous, intraperitoneal, etc.), eye dropping, instillation, percutaneous administration, oral administration, inhalation, and the like.

Also, the dosage form such as injectable preparations (solutions, suspensions, emulsions, solids to be dissolved when used, etc.), tablets, capsules, granules, powders, liquids, liposome inclusions, ointments, gels, external powders, sprays, inhalating powders, eye drops, eye ointments, suppositories, pessaries, and the like can be selected appropriately depending on the administration method, and the peptide of the present invention can be accordingly formulated.

The dose of the medicine of the present invention should be set up individually depending on the purpose of administration (prevention, maintenance (prevention of aggravation), alleviation (improvement of symptom) or cure); the kind of disease; the symptom, sexuality and age of patient; the administration method and the like and is not limited particularly.

Hereafter, representative medicine will be explained.

<3-1> Antimicrobial Medicine

The antimicrobial medicine is a medicine which comprises the antimicrobial agent of the present invention (hereafter, referred to as the antimicrobial medicine of the present invention) and contains the peptide of the present invention as an active ingredient.

The antimicrobial agent of the present invention, as stated above, has a potent antimicrobial activity on gram-positive and gram-negative bacteria. Therefore, the antimicrobial medicine of the present invention can be applied to various gram-positive and gram-negative bacteria. The bacteria which are the target of application are not limited particularly but *Escherichia coli*, Klebsiella, Salmonella, and the like are preferred as the gram-negative bacteria, and *Staphylococcus aureus* and the like are preferred as the gram-positive bacteria.

Also, the antimicrobial medicine of the present invention can be used on multiple drug resistant gram-positive bacteria (for example, methicillin-resistant *Staphylococcus aureus* (MRSA), methicillin-sensitive *Staphylococcus aureus* (MSSA), vancomycin-resistant enterococci, etc.) and multiple drug resistant gram-negative bacteria (multiple drug resistant Helicobacter, Shigella, Salmonella, etc.).

The antimicrobial medicine of the present invention exhibits a potent antimicrobial activity on *Escherichia coli*, particularly pathogenic *Escherichia coli* O-157, *Staphylococcus aureus*, particularly methicillin-resistant *Staphylococcus aureus* (MRSA), and methicillin-sensitive *Staphylococcus aureus* (MSSA), so that it is more preferred that these bacteria be the target of application.

The antimicrobial medicine of the present invention may consist of the peptide of the present invention alone or may be in the form of a composition comprising the peptide of the present invention and a pharmaceutically acceptable carrier. The pharmaceutically acceptable carrier which can be used is not limited particularly and includes an excipient, a binder, a lubricant, a colorant, a disintegrant, a buffer, an isotonic agent, a preservative, an anesthetic, and the like which can be used in a medical field. Also, it may be used in combination with another antimicrobial medicine such as lysozyme, antibiotics, and the like.

The antimicrobial medicine of the present invention can be used for the treatment of, for example, the part infected with microorganisms outside the body or for the treatment of microbial infection inside the body, and an appropriate administration method therefore can be selected depending on the purpose of treatment, from injection (subcutaneous, intracutaneous, intravenous, intraperitoneal, etc.), eye dropping, instillation, percutaneous administration, oral administration, inhalation, etc.

Also, the dosage form such as injectable preparations (solutions, suspensions, emulsions, solids to be dissolved when used, etc.), tablets, capsules, granules, powders, liquids, liposome inclusions, ointments, gels, external powders, sprays, inhalating powders, eye drops, eye ointment, suppositories, pessaries, and the like can be appropriately selected depending on the administration method, and the antimicrobial medicine of the present invention can be accordingly formulated.

The dose of the antimicrobial medicine of the present invention should be set up individually depending on the kind of bacteria; the state of infection; the symptom, sexuality age of patient; the administration method; and the like and is not limited particularly. The antimicrobial medicine of the present invention may be administered in a dose per time of about 5 to 15 (mg/kg body weight) as the peptide of the present invention for an adult person.Among the peptides of the present invention used in the antimicrobial medicine of the present invention, the peptide having any one of the following amino acid sequences (a) to (f) has high antimicrobial activity as is apparent from the Examples described below in which its antimicrobial activity is shown specifically and thus is preferred.

(a)
Phe Arg Lys Ser Lys Glu Lys Ile Gly Lys Leu Phe Lys Arg Ile Val Gln Arg Ile Lys Asp Phe Leu Arg Asn Leu Val (SEQ ID NO: 2), (b)
Phe Arg Lys Ser Lys Glu Lys Ile Gly Lys Leu Phe Lys Arg Ile Val Gln Arg Ile Leu Asp Phe Leu Arg Asn Leu Val (SEQ ID NO: 3), (c)
Phe Arg Lys Ser Lys Glu Lys Ile Gly Lys Phe Phe Lys Arg Ile Val Gln Arg Ile Phe Asp Phe Leu Arg Asn Leu Val (SEQ ID NO: 4), (d)
Glu Lys Ile Gly Lys Leu Phe Lys Arg Ile Val Gln Arg Ile Leu Asp Phe Leu Arg Asn Leu Val (SEQ ID NO: 5), (e)
Lys Leu Phe Lys Arg Ile Val Gln Arg Ile Leu Asp Phe Leu Arg Asn Leu Val (SEQ ID NO: 6), and (f)
Lys Leu Phe Lys Arg Ile Val Lys Arg Ile Leu Lys Phe Leu Arg Lys Leu Val (SEQ ID NO: 7).Also, among the peptides having the amino acid sequences (a) to (f), the peptide having the amino acid sequence (e) or (f) exhibits a very high antimicrobial activity on both gram-negative and gram-positive bacteria and thus is particularly preferred.

<3-2> Bacterial Infection-Treating Agent of the Present InventionThe bacterial infection-treating agent of the present invention is a bacterial infection-treating agent which comprises the peptide of the present invention as an active ingredient.Because of its potent antimicrobial activity onto the gram-positive and gram-negative bacteria of the peptide of the present invention serving as the active ingredient thereof, the bacterial infection-treating agent of the present invention can be applied to bacterial infections caused by gram-positive and gram-negative bacteria. The bacteria which cause the bacterial infections are not limited particularly but bacterial infections caused by *Escherichia coli*, Klebsiella, Salmonella, and the like are preferred as the gram-negative bacteria-caused infection and bacterial infections caused by *Staphylococcus aureus*, and the like are preferred as the gram-positive bacteria-caused infection.Also, the bacterial infection-treating agent of the present invention can be used on multiple drug resistant gram-positive bacteria (for example, methicillin-resistant *Staphylococcus aureus* (MRSA), methicillin-sensitive *Staphylococcus aureus* (MSSA), vancomycin-resistant enterococci, etc.) and multiple drug resistant gram-negative bacteria (multiple drug resistant Helicobacter, Shigella, Salmonella, etc.). The bacterial infection-treating agent of the present invention exhibits a potent antimicrobial activity on *Escherichia coli*, particularly pathogenic *Escherichia coli* O-157 and *Staphylococcus aureus*, particularly methicillin-sensitive *Staphylococcus aureus* (MRSA), so that it is more preferred that these bacterial infections be the target of application.It is sufficient for the bacterial infection-treating agent of the present invention to comprise at least the peptide of the present invention. For example, the bacterial infection-treating agent of the present invention may consist of the peptide of the present invention alone or may be in the form of a composition comprising the peptide of the present invention and a pharmaceutically acceptable carrier. The administration method of the bacterial infection-treating agent of the present invention can be selected appropriately as in the case of the above-described antimicrobial medicine of the present invention, and injection (subcutaneous, intracutaneous, intravenous, intraperitoneal, etc.) is preferred.Also, the dosage form of the bacterial infection-treating agent of the present invention can be selected appropriately depending on the administration method as in the case of the antimicrobial medicine of the present invention, and the bacterial infection-treating agent is preferably formulated into injectable preparations (solutions, suspensions, emulsions, solids to be dissolved when used, etc.).The dose of the bacterial infection-treating agent of the present invention should be set up individually depending on the kind of bacteria; the state of infection; the symptom, sexuality and age of patient; the administration method and the like and is not limited particularly. The bacterial infection-treating agent of the present invention may be administered in a dose per time of about 5 to 15 (mg/kg body weight) as the peptide of the present invention for an adult person.Among the peptides of the present invention used in the bacterial infection-treating agent of the present invention, the peptide having any one of the following amino acid sequences (a) to (f) has a high antimicrobial activity as is apparent from the Examples described below in which its antimicrobial activity is specifically shown and thus is preferred.

(a)
Phe Arg Lys Ser Lys Glu Lys Ile Gly Lys Leu Phe Lys Arg Ile Val Gln Arg Ile Lys Asp Phe Leu Arg Asn Leu Val (SEQ ID NO: 2), (b)
Phe Arg Lys Ser Lys Glu Lys Ile Gly Lys Leu Phe Lys Arg Ile Val Gln Arg Ile Leu Asp Phe Leu Arg Asn Leu Val (SEQ ID NO: 3), (c)
Phe Arg Lys Ser Lys Glu Lys Ile Gly Lys Phe Phe Lys Arg Ile Val Gln Arg Ile Phe Asp Phe Leu Arg Asn Leu Val (SEQ ID NO: 4), (d)
Glu Lys Ile Gly Lys Leu Phe Lys Arg Ile Val Gln Arg Ile Leu Asp Phe Leu Arg Asn Leu Val (SEQ ID NO: 5), (e)
Lys Leu Phe Lys Arg Ile Val Gln Arg Ile Leu Asp Phe Leu Arg Asn Leu Val (SEQ ID NO: 6), and (f)
Lys Leu Phe Lys Arg Ile Val Lys Arg Ile Leu Lys Phe Leu Arg Lys Leu Val (SEQ ID NO: 7).Also, among the peptides having the amino acid sequences (a) to (f), the peptide having the amino acid sequence (e) or (f) exhibits a very high antimicrobial activity on both gram-negative and gram-positive bacteria and thus is particularly preferred.

<3-3> Endotoxin Shock Suppressant of the Present InventionThe endotoxin shock suppressant of the present invention is an endotoxin shock suppressant which comprises the peptide of the present invention as an active ingredient.The endotoxin shock suppressant of the present invention has an excellent suppressing effect on endotoxin shock accompanying sepsis, endotoxin shock accompanying gram-negative infections, or the like and also has an effect of suppressing lethality due to such an endotoxin shock.It is sufficient for the endotoxin shock suppressant of the present invention to comprise at least the peptide of the present invention. For example, the endotoxin shock suppressant of the present invention may consist of the peptide of the present invention alone or may be in the form of a composition comprising the peptide of the present invention and a pharmaceutically acceptable carrier. The pharmaceutically acceptable carrier, the administration method, the dosage form, the dose, and the like which can be used are the same as the above-described bacterial infection-treating agent of the present invention. Among the peptides of the present invention, preferred as the endotoxin shock suppressant of the present invention includes the peptide having any one of following amino acid sequences (a) to (d) and (f).

(a)
Phe Arg Lys Ser Lys Glu Lys Ile Gly Lys Leu Phe Lys Arg Ile Val Gln Arg Ile Lys Asp Phe Leu Arg Asn Leu Val (SEQ ID NO: 2), (b)
Phe Arg Lys Ser Lys Glu Lys Ile Gly Lys Leu Phe Lys Arg Ile Val Gln Arg Ile Leu Asp Phe Leu Arg Asn Leu Val (SEQ ID NO: 3), (c)
Phe Arg Lys Ser Lys Glu Lys Ile Gly Lys Phe Phe Lys Arg Ile Val Gln Arg Ile Phe Asp Phe Leu Arg Asn Leu Val (SEQ ID NO: 4), (d)
Glu Lys Ile Gly Lys Leu Phe Lys Arg Ile Val Gln Arg Ile Leu Asp Phe Leu Arg Asn Leu Val (SEQ ID NO: 5) and (f)
Lys Leu Phe Lys Arg Ile Val Lys Arg Ile Leu Lys Phe Leu Arg Lys Leu Val (SEQ ID NO: 7).Also, a more preferred peptide of the present invention as the endotoxin shock suppressant of the present invention has any one of the amino acid sequences (b) to (d) and (f) and the most preferred peptide of the present invention has any one of the amino acid sequence (b), (c) and (f).

<4> Endotoxin-Removing Agent of the Present Invention-The endotoxin-removing agent of the present invention is an endotoxin-removing agent comprising the peptide of the present invention immobilized to an insoluble carrier. The endotoxin-removing agent of the present invention is based on application of a high endotoxin bindability of the peptide of the present invention to adsorption and removal of endotoxin.The shape of the insoluble carrier to which the peptide of the present invention is immobilized is not limited particularly and there can be cited various forms, for example, forms of membrane (filter type, hollow type, tube type, flat membrane type, etc.), granule, latex, chip, powder, and microplate.The material of the insoluble carrier is not limited particularly either and there can be cited various materials, for example, polystyrene materials, polypropylene materials, polyamide materials, cellulose materials, agarose materials, polyacrylamide materials, dextran materials, and vinyl polymer materials.The method for immobilizing the peptide of the present invention to the insoluble carrier is not limited particularly either and the immobilization of the peptide of the present invention can be achieved by utilizing general methods used as a preparation method for immobilized enzymes such as a physical adsorption method, an ionic bond method, a covalent bond method, an inclusion method. (KOTEIKA KOSO (Immobilized Enzymes), 1975, Kodansha, pages 9–75).For example, for the insoluble carriers made of polystyrene materials or polypropylene materials, the peptide of the present invention can be physically immobilized. Also, for example, the insoluble carriers made of polyamide materials, cellulose materials, agarose materials, polyacrylamide materials, dextran materials, or vinyl polymer materials, the peptide of the present invention can be chemically immobilized. As the chemical immobilizing (binding) method, there can be cited, for example, a diazotization method in which diazo coupling is carried out utilizing an aromatic amino group in the insoluble carrier, a CNBr method in which a peptide bond is formed by activating a hydroxyl group in the insoluble carrier with CNBr, an acid azide method in which a peptide bond is formed by using a hydrazine derivative of the insoluble carrier, an alkylation method in which a peptide is alkylated utilizing a reactive functional group such as a halogen in the insoluble carrier, a cross linking method in which a crosslinking agent reactive with a free amino group such as glutaraldehyde crosslinks between the insoluble carrier and the free amino group in the peptide, a carbodiimide method, an epoxy activation method, and methods in which a bond is formed through a spacer using one of the above-described methods. An appropriate method can be selected from these known methods depending on the kind of the insoluble carrier for application in bonding of peptide of the present invention.The insoluble carrier to which the peptide of the present invention is immobilized is brought into contact with a solution in which removal of endotoxin is desired to form a complex of the endotoxin in the solution and the insoluble carrier to which the peptide of the present invention is immobilized, and then the complex thus formed is removed, whereby the endotoxin in the solution can be removed.The method for contacting the insoluble carrier to which the peptide of the present invention is immobilized with the solution in which removal of endotoxin is desired is not limited particularly and known solid-liquid contacting means can be used. For example, a method in which a solution is passed through a filter-shaped or hollow fiber-shaped insoluble carrier or over a flat membrane-shaped insoluble carrier, a method in which a solution is passed through a column charged with a granular insoluble carrier, a method in which a solution is charged in a microplate-shaped well and the solution is left to stand for a certain time and then the solution is separated, a method in which a solution is added onto an insoluble carrier of any shape and shaken or left to stand for a certain time and then usual solid-liquid separation means (filtration, centrifugation, aspiration, decantation, etc.) can be used to obtain a solution which is free of endotoxin, or the like.The solution in which removal of endotoxin is desired is not limited particularly and examples thereof include solutions used in a pharmaceutical production plant, a medical installation, and the like, more particularly, dialysate fluid, parenteral fluid, blood, pharmaceuticals, superpure water, and the like but not limited thereto.The insoluble carrier to which the peptide of the present invention is immobilized is preferably free of endotoxin.The peptide of the present invention is a partial peptide corresponding to a known partial peptide of human-derived antimicrobial protein (CAP18) whose specified amino acid residue is substituted, and exhibits an endotoxin-binding activity, an antimicrobial activity, an endotoxin-neutralizing activity, which are significantly higher that those of the known partial peptide, so that it is extremely useful as an active ingredient of an antimicrobial agent, a bacterial infection-treating agent, an endotoxin shock suppressant, an endotoxin-removing agent, and the like.

Since the peptide of the present invention has a very high pharmacological activity as described above, the amount of the active ingredient in medicines such as the antimicrobial medicine of the present invention, the bacterial infection-treating agent of the present invention, and the endotoxin shock suppressant of the present invention which contain the peptide of the present invention as the active ingredient, can be reduced, whereby the medicine of the present invention which is safe and inexpensive can be provided. Also, since the peptide of the present invention is based on the partial peptide derived from humans, the medicine of the present invention is extremely useful as a medicine which is highly safe particularly to humans.

Further, making the best of the very high endotoxin-binding activity of the peptide of the present invention, there can be provided an endotoxin-removing agent containing the peptide of the present invention immobilized to an insoluble carrier and an endotoxin-determining agent containing the peptide of the present invention.

EXAMPLES

Hereafter, the invention will be described in more detail by examples.

Example 1

<1> Preparation of Peptide of the Present Invention

The peptides of the present invention having an amino acid sequence selected from (a) to (f) set forth below were produced according to a solid phase synthesis method, by entrusting the production to Peptide Institute, Inc.

(a) (27-mer, substituted)
Phe Arg Lys Ser Lys Glu Lys Ile Gly Lys Leu Phe Lys Arg Ile Val Gln Arg Ile Lys Asp Phe Leu Arg Asn Leu Val (SEQ ID NO: 2), (b) (27-mer, substituted)
Phe Arg Lys Ser Lys Glu Lys Ile Gly Lys Leu Phe Lys Arg Ile Val Gln Arg Ile Leu Asp Phe Leu Arg Asn Leu Val (SEQ ID NO: 3), (c) (27-mer, substituted)
Phe Arg Lys Ser Lys Glu Lys Ile Gly Lys Phe Phe Lys Arg Ile Val Gln Arg Ile Phe Asp Phe Leu Arg Asn Leu Val (SEQ ID NO: 4), (d) (22-mer, substituted)
Glu Lys Ile Gly Lys Leu Phe Lys Arg Ile Val Gln Arg Ile Leu Asp Phe Leu Arg Asn Leu Val (SEQ ID NO: 5), (e) (18-mer, substituted)
Lys Leu Phe Lys Arg Ile Val Gln Arg Ile Leu Asp Phe Leu Arg Asn Leu Val (SEQ ID NO: 6), and (f) (18-mer, substituted)
Lys Leu Phe Lys Arg Ile Val Lys Arg Ile Leu Lys Phe Leu Arg Lys Leu Val (SEQ ID NO: 7).

For comparison, peptides A1, A3, A5, A6 and A7 set forth below whose amino acids were not substituted (known; unsubstituted) were produced according to a solid phase synthesis method, by entrusting the production to Peptide Institute, Inc.

A1 (27-mer, unsubstituted)
Phe Arg Lys Ser Lys Glu Lys Ile Gly Lys Glu Phe Lys Arg Ile Val Gln Arg Ile Lys Asp Phe Leu Arg Asn Leu Val (SEQ ID NO: 8)

A3 (22-mer, unsubstituted)
Glu Lys Ile Gly Lys Glu Phe Lys Arg Ile Val Gln Arg Ile Lys Asp Phe Leu Arg Asn Leu Val (SEQ ID NO: 9)

A5 (24-mer, unsubstituted)
Ser Lys Glu Lys Ile Gly Lys Glu Phe Lys Arg Ile Val Gln Arg Ile Lys Asp Phe Leu Arg Asn Leu Val (SEQ ID NO: 10)

A6 (23-mer, unsubsituted)
Lys Glu Lys Ile Gly Lys Glu Phe Lys Arg Ile Val Gln Arg Ile Lys Asp Phe Leu Arg Asn Leu Val (SEQ ID NO: 11)

A7 (18-mer, unsubsituted)
Lys Glu Phe Lys Arg Ile Val Gln Arg Ile Lys Asp Phe Leu Arg Asn Leu Val (SEQ ID NO: 12)

Table 1 shows the relationships between the peptide of the present invention (a) to (f) and known peptides A1, A3, A5, A6, and A7. In Table 1, amino acid residues were indicated by respective single character symbols. Also, substituted amino acid residues were underlined.

TABLE 1

| | | | |
|---|---|---|---|
| (27-mer) | A1 | FRKSKEKIGKEFKRIVQRIKDFLRNLV | (SEQ ID NO: 8) |
| | (a) | FRKSKEKIGK_L_FKRIVQRIKDFLRNLV | (SEQ ID NO: 2) |
| | (b) | FRKSKEKIGK_L_FKRIVQRIL_D_F_L_RNLV | (SEQ ID NO: 3) |
| | (c) | FRKSKEKIGK_F_FKRIVQRI_F_DFLRNLV | (SEQ ID NO: 4) |
| (24-mer) | A5 | SKEKIGKEFKRIVQRIKDFLRNLV | (SEQ ID NO: 10) |
| (23-mer) | A6 | KEKIGKEFKRIVQRIKDFLRNLV | (SEQ ID NO: 11) |
| (22-mer) | A3 | EKIGKEFKRIVQRIKDFLRNLV | (SEQ ID NO: 9) |
| | (d) | EKIGK_L_FKRIVQRI_L_DFLRNLV | (SEQ ID NO: 5) |
| (18-mer) | A7 | KEFKRIVQRIKDFLRNLV | (SEQ ID NO: 12) |
| | (e) | K_L_FKRIVQRI_L_DFLRNLV | (SEQ ID NO: 6) |
| | (f) | K_L_FKRIV_K_RI_L_KFLR_K_LV | (SEQ ID NO: 7) |

For the peptides A1, (b), A3, (d), A5, and A6 from among the above-described, produced peptides, (1) amino acid analytical values (hydrolysis conditions: 6 N HCl, 110° C., 22 hours) and (2) purity (%; calculated from high performance liquid chromatography data) are shown in Table 2. In each elution pattern of these peptide by high performance liquid chromatography (reversed-phase chromatography), there was observed a single peak. The conditions of the chromatography were as follows.

Column: YMC Pak ODS-AM (4.6 mm I.D.×150 mm) (YMC Co., Ltd.)

Eluent: For A1, 20–70% acetonitrile/0.1% trifluoroacetic acid; 25 minutes For others, 30–80% acetonitrile/0.1% trifluoroacetic acid; 25 minutes Flow rate: 1.0 ml/minute Temperature: For A1, A3, A5 and A6, 25° C. For others, 50° C.

Detection wavelength: 220 nm

TABLE 2

| Peptide | Amino acid analytical value (theoretical value in parenthesis) | Purity (%) |
|---|---|---|
| A1 | Asp(2)1.97, Ser(1)0.98, Glu(3)3.02, Gly(1)0.95, Val(2)1.63, Ile(3)2.45, Leu(2)2.03, Phe(3)3.00, Lys(6)5.91, NH$_3$(2)2.03, Arg(4)3.99 | 97.3 |
| (b) | Asp(2)2.00, Ser(1)0.94, Glu(2)2.03, Gly(1)0.96, Val(2)1.66, Ile(3)2.49, Leu(4)4.07, Phe(3)3.02, Lys(5)5.00, NH$_3$(2)2.08, Arg(4)4.00 | 97.0 |
| A3 | Asp(2)2.00, Glu(3)3.11, Gly(1)0.96, Val(2)1.66, Ile(3)2.48, Leu(2)2.04, Phe(2)2.02 Lys(4)3.96, NH$_3$(2)1.92, Arg(3)3.00 | 97.6 |

TABLE 2-continued

| Peptide | Amino acid analytical value (theoretical value in parenthesis) | Purity (%) |
|---|---|---|
| (d) | Asp(2)1.97, Glu(2)2.05, Gly(1)0.95, Val(2)1.63, Ile(3)2.47, Leu(4)4.00, Phe(2)2.00 Lys(3)2.97, NH₃(2)1.91, Arg(3)2.95 | 99.2 |
| A5 | Asp(2)1.98, Ser(1)0.95, Glu(3)3.00, Gly(1)0.95, Val(2)1.65, Ile(3)2.47, Leu(2)2.03, Phe(2)2.00, Lys(5)4.92, NH₃(2)1.99, Arg(3)2.98 | 98.0 |
| A6 | Asp(2)2.00, Glu(3)3.09, Glu(1)0.96, Val(2)1.66, Ile(3)2.48, Leu(2)2.05, Phe(2)2.02 Lys(5)4.96, NH₃(2)1.92, Arg(3)3.00 | 98.1 |

The produced peptides were each a white lyophilized preparation.

From the results, it is considered that each produced peptide has a purity of 97% or more and shows a single peak by high performance liquid chromatography (reversed-phase chromatography). Also, the amino acid analytical values were shown to well coincide with theoretical values obtained from the amino acid sequence, which indicated that the peptide was produced correctly.

The peptides of the present invention (a) to (f) are common in that they each contain at least the following amino acid sequence and further in that they have an LPS-binding activity, an antimicrobial activity, and an endotoxin-neutralizing activity as is described later on.

Therefore, the peptide of the present invention is generalized as a peptide containing at least the following amino acid sequence (SEQ ID NO: 1):

Lys Xa1 Phe Lys Arg Ile Val Xa2 Arg Ile Xaa Xa2 Phe Leu Arg Xa2 Leu Val wherein, Xa1 represents a hydrophobic amino acid residue, each of Xa2 independently represents a hydrophilic amino acid residue, and Xaa represents an arbitrary amino acid residue.

<2> LPS-Binding Activity

Measurement method for LPS-binding activity: To 1.0 ml of 1% sheep erythrocyte suspension, 0.2 ml of a solution (100 μg/ml) of Re-type LPS (Re-LPS; manufactured by List Lab Co.) drived from *Salmonella minnesota* was added, and the mixture was incubated at 37° C. for 30 minutes and subjected to centrifugal washing with phosphate buffered saline (PBS) to prepare 1% LPS-sensitized erythrocyte. To 50 μl of serial twofold-diluted sample (peptide), 50 μl of the LPS-sensitized erythrocyte was added, and the mixture was incubated in a U-type microplate (γ-ray-sterilized; manufactured by Nunc Co.) at 37° C. for 1 hour. Maximum dilution fold of the sample at which agglutination reaction occurs was obtained and the concentration calculated therefrom was defined as minimum agglutinating concentration (MAC). The lower the value of MAC, the stronger the LPS-binding activity of the sample.

2-1. Effect of Substitution of Amino Acid Residue (1)

A1, the peptide of the present invention (b), A3 and the peptide of the present invention (d) were used as samples and their LPS-binding activities were examined by the above-described measurement method. The results are shown in Table 3.

TABLE 3

| | LPS-Binding Activity (MAC) | |
|---|---|---|
| Sample | μg/mL | μM |
| 27-mer | | |
| A1 (unsubstituted form) | 3.1 | 0.9 |
| Peptide of the present invention (b) (substituted form) | 0.2 | 0.06 |
| 22-mer | | |
| A3 (unsubstituted form) | 25.0 | 9.2 |
| Peptide of the present invention (d) (substituted form) | 0.8 | 0.3 |

From table 3, it was revealed that the peptide of the present invention (substituted form) had an LPS-binding activity by about 15 to 31 folds higher than the unsubstituted form (known).

2-2. Effect of Substitution of Amino Acid Residue (2)

A1, the peptides of the present invention (b), (a) and (c) were used as samples and their LPS-binding activities were examined by the above-described measurement method. The results are shown in Table 4.

TABLE 4

| Sample | LPS-Binding Activity (MAC) μg/mL |
|---|---|
| 27-mer | |
| A1 (unsubstituted form) | 6.3 |
| Peptide of the present invention (b) (substituted form) | 0.4 |
| Peptide of the present invention (a) (substituted form) | 0.8 |
| Peptide of the present invention (c) (substituted form) | 0.4 |

Table 4 reveals that the peptide of the present invention (substituted form) had an LPS-binding activity by about 8 to 16 folds higher than the unsubstituted form (known).

2-3. LPS-Binding Activity of Modified Peptide

Peptides having acetylated N-terminal and amidated C-terminal (A7, the peptide of the present invention (e) and the peptide of the present invention (f)) were used as samples and the LPS-binding activities thereof were examined by the above-described measurement method. The results are shown in Table 5.

TABLE 5

| Sample | LPS-Binding Activity (MAC) μg/mL |
|---|---|
| 18-mer | |
| A7 (unsubstituted form) | 12.5 |
| Peptide of the present invention (e) (substituted form) | 0.4 |
| Peptide of the present invention (f) (substituted form) | 0.1 |

Table 5 reveals that the modified peptide of the present invention (substituted form) had an LPS-binding activity by about 31 to 125 folds higher than the unsubstituted form (known). The LPS-binding activity was given no influence by the modification of peptide.

<3> Pharmacological Tests
3-1. Antimicrobial Activity

Measurement method for antimicrobial activity: For the measurement of antimicrobial activity, E. coli [E. coli O157:H7 (collected from an E. coli O157 patients in Okayama prefecture, Kanagawa prefecture and Morioka city of Iwate Prefecture)], Klebsiella or Methicillin resistant *Staphylococcus aureus*; MRSA] was used.

These bacteria were grown in a liquid medium (Tryptosoy broth; manufactured by Eiken Kagaku). The bacteria cells in a logarithmic growth phase were collected, washed with PBS (pH 7.2), and adjusted to a final concentration of $5 \times 10^3$ to $1 \times 10^4$ cells/ml. To 450 μl of cell suspension, 50 μl of samples (peptide) in various concentrations were each added and mixtures were incubated at 37° C. for 1 hour. After the incubation, 100 μl of each reaction mixture was spread on an agarose medium (Nutrient agar; manufactured by Eiken Kagaku). This was incubated at 37° C. for 24 hours and the colony-forming unit (CFU) was counted to obtain 50% inhibition concentration ($IC_{50}$).

3-1-1. Antimicrobial Activity on E. coli (E. coli O157) (1)

Polymyxin B (known antimicrobial agent), A1, the peptide of the present invention (b), A3, the peptide of the present invention (d), A5 and A6 were used as samples and their antimicrobial activities on E. coli [E. coli O157:H7 (collected from E. coli O157 patients in Okayama prefecture, Kanagawa prefecture and Morioka city of Iwate Prefecture)] were examined by the above-described measurement method. The results are shown in Table 6.

TABLE 6

| Sample | Antimicrobial Activity on E. Coli O157:H7 ($IC_{50}$); μg/mL | | |
|---|---|---|---|
| | Okayama | Kanagawa | Morioka |
| Polymyxin B | 0.2 | <2.5 | NT |
| 27-mer | | | |
| A1 (unsubstituted form) | >10 | 14 | >20 |
| Peptide of the present invention (b) (substituted form) | 0.8 | <2.5 | 1.3 |
| 22-mer | | | |
| A3 (unsubstituted form) | >10 | 35 | >20 |
| Peptide of the present invention (d) (substituted form) | 2.3 | <2.5 | 3.0 |
| 24-mer | | | |
| A5 (unsubstituted form) | NT | >20 | NT |
| 23-mer | | | |
| A6 (unsubstituted form) | NT | >20 | NT |

In the table above, NT indicates that no test was performed.

Table 6 reveals that that the peptide of the present invention (substituted form) had an antimicrobial activity on E. coli O157:H7 by about 4 to 15 folds higher than the unsubstituted form (known).

The results show that although the activity is identical with polymyxin B, the peptide of the present invention is advantageous to polymyxin B since polymyxin B has strong toxicity.

3-1-2. Antimicrobial Activity on E. coli (E. coli O157) (2)

A1, the peptide of the present invention (b), the peptide of the present invention (a) and the peptide of the present invention (c) were used as samples and their antimicrobial activities on E. coli (E. coli O157:H7 (collected from E. coli O157 patients in Okayama prefecture)) were examined by the above-described measurement method. Their results are shown in Table 7.

TABLE 7

| Sample | Antimicrobial Activity on E. Coli O157:H7 ($IC_{50}$); μg/mL |
|---|---|
| 27-mer | |
| A1 (unsubstituted form) | >10 |
| Peptide of the present invention (b) (substituted form) | 0.8 |
| Peptide of the present invention (a) (substituted form) | 1.2 |
| Peptide of the present invention (c) (substituted form) | 0.7 |

Table 7 reveals that the peptide of the present invention (substituted form) had an antimicrobial activity on E. coli O157:H7 by about 8 to 14 folds higher than the unsubstituted form (known).

3-1-3. Antimicrobial Activity on Various Gram-Negative and Gram-Positive Bacteria (1)

Polymyxin B (known antimicrobial agent), A1, the peptide of the present invention (b), A3, and the peptide of the present invention (d), (each in a concentration of 20 μg/ml) were used as samples and the colony-forming unit (CFU) of a gram-negative bacterium (E. coli O157:H7 or Klebsiella) and a gram-positive bacterium (methicillin-resistant *Staphylococcus aureus* (MRSA)) was counted by the above-described method for the measurement of antimicrobial activity. Taking CFU when no sample was added (concentration: 0 μg/ml) as 100%, a relative value of CFU was obtained and the value of 100% minus the relative value of CFU was calculated and defined as a value of the antimicrobial activity. The results are shown in FIG. 5.

Figure 5:
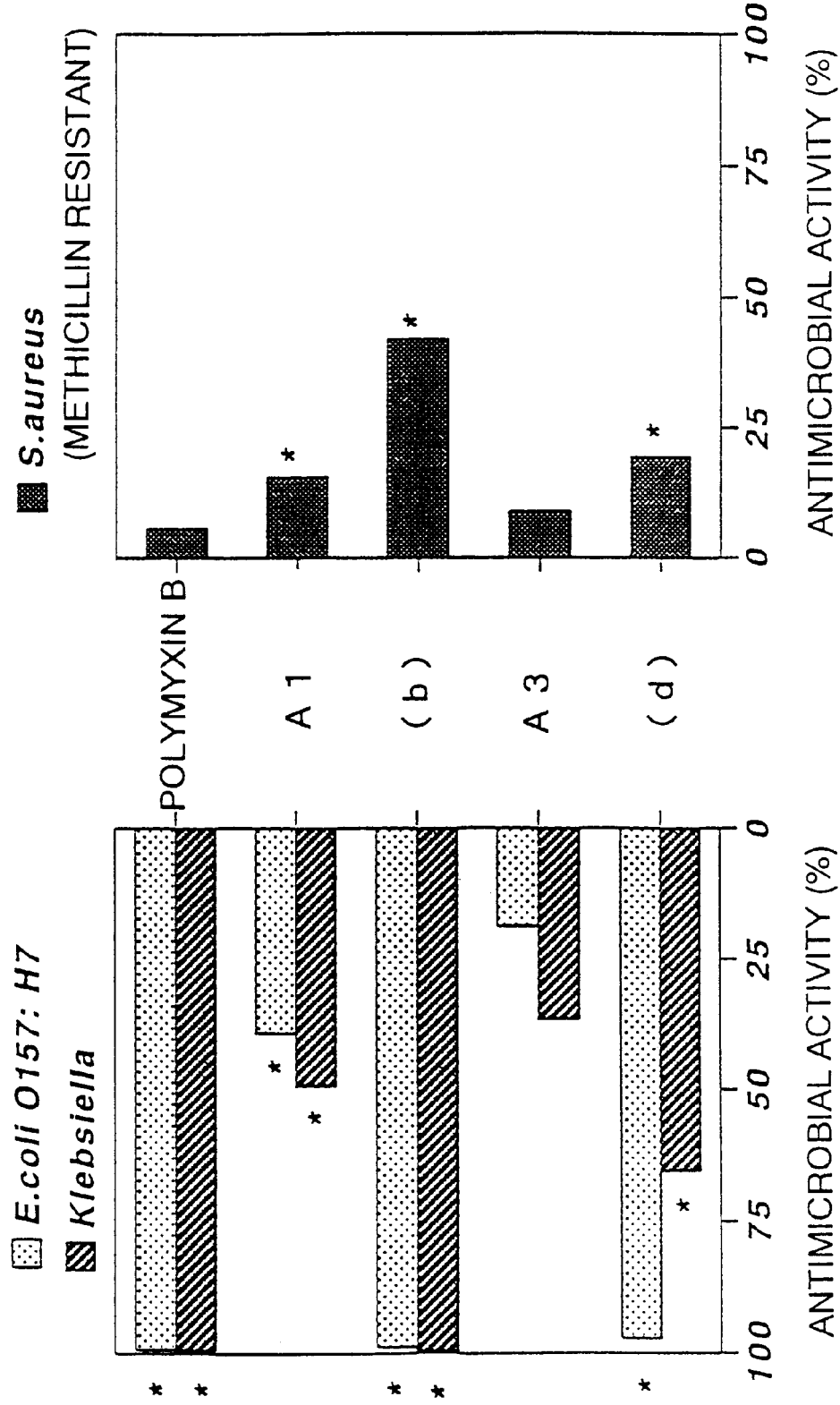
FIG. 5 shows antimicrobial activities of polymyxin B and peptides (A1, (b), A3 and (d)) produced in Example 1 on various bacteria.

In FIG. 5, the symbol * means a significant difference at $p<0.05$ for the results obtained using PBS instead of a sample (peptide).

FIG. 5 shows that the peptide of the present invention (substituted form) is significantly higher in the antimicrobial activity than the unsubstituted form (known) and exhibits the antimicrobial activity on both gram-negative and gram-positive bacteria. Also, it shows that the peptides of the present invention (b) and (d) exhibit a potent antimicrobial activity particularly on gram-negative bacteria.

3-1-4. Antimicrobial Activity on Various Gram-Negative and Gram-Positive Bacteria (2)

A7, the peptide of the present invention (e) and the peptide of the present invention (f) (each in a concentration of 20 μg/ml) were used as samples and the colony-forming unit (CFU) of a gram-negative bacterium (E. coli or *Salmonella typhimurium*) and a gram-positive bacterium (methicillin-sensitive *Staphylococcus aureus* (MSSA) or methicillin-resistant *Staphylococcus aureus* (MRSA)) was counted in the same manner as the above-described method for the measurement of antimicrobial activity. Taking CFU when no sample was added (concentration: 0 μg/ml) as 100%, a relative value of CFU was obtained and the value of 100% minus the relative value of CFU was calculated and defined as a value of antimicrobial activity. The results are shown in FIG. 6.

Figure 6:
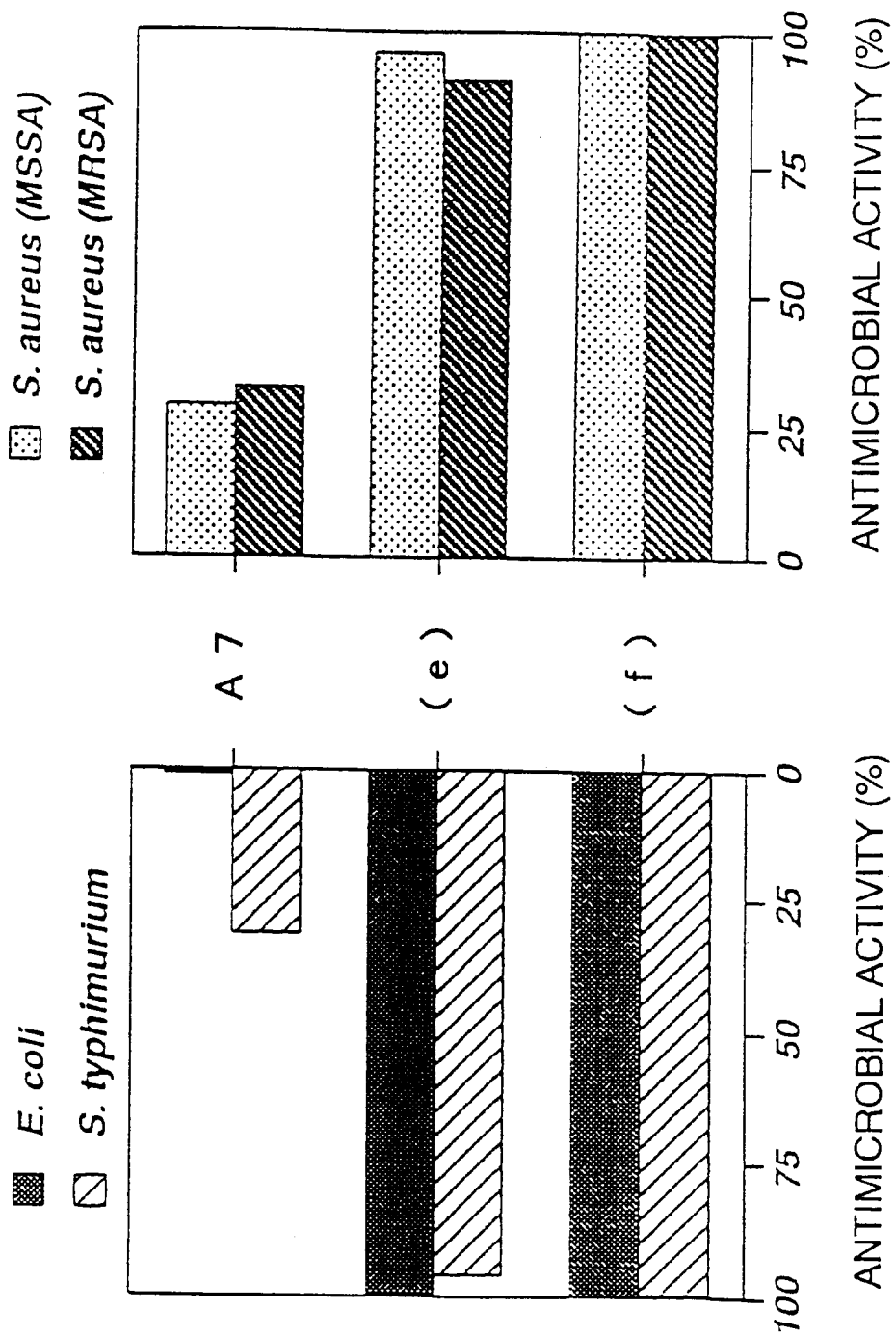
FIG. 6 shows antimicrobial activities of peptides (A7, (e) and (f)) produced in Example 1 on various bacteria.

FIG. 6 shows that the peptide of the present invention (substituted form) is significantly higher in the antimicrobial activity than the unsubstituted form (known) and that the peptides of the present invention (e) and (f) exhibit a potent antimicrobial activity on both gram-negative and gram-positive bacteria.

Figure 7:
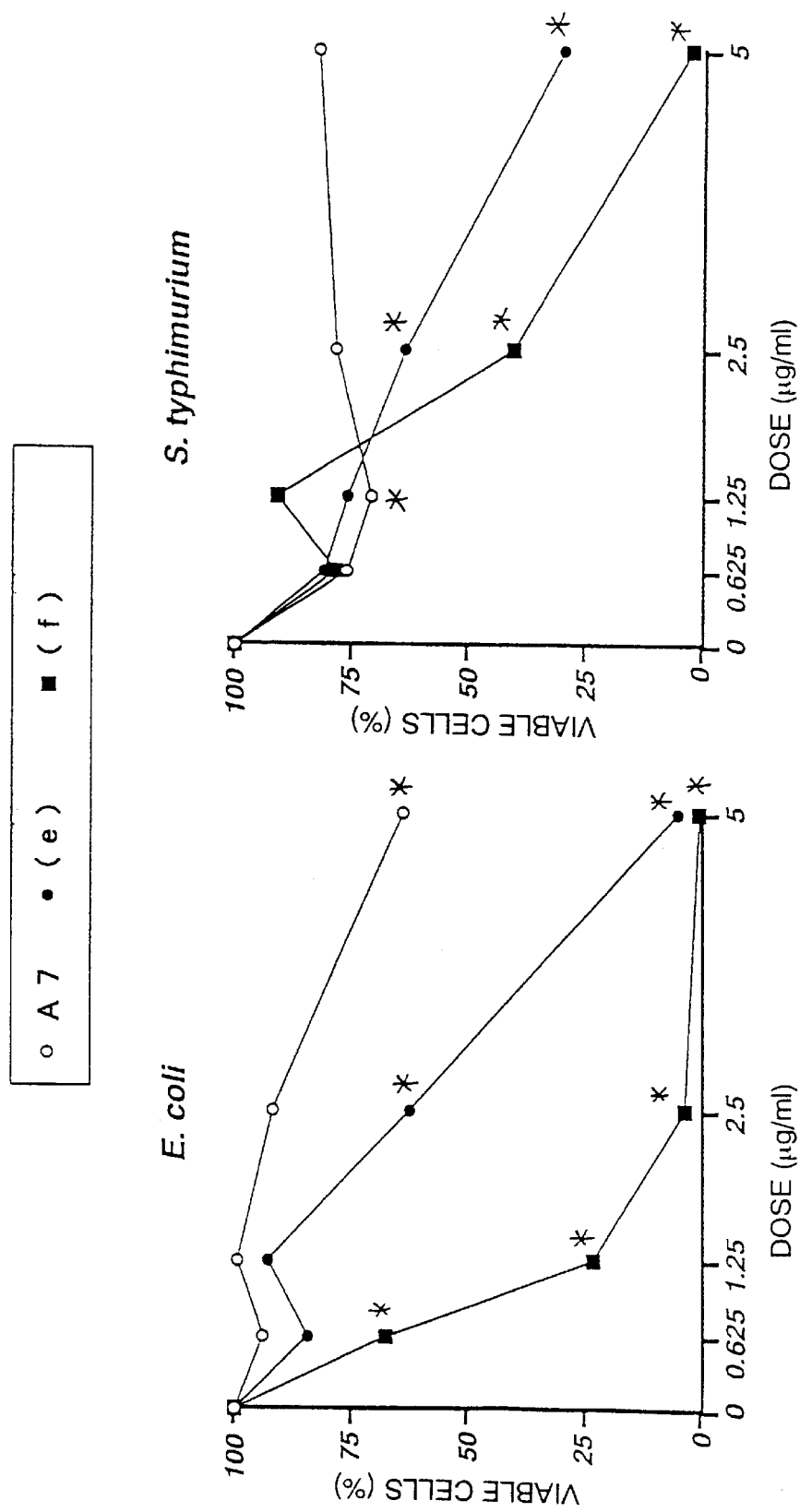
FIG. 7 shows relationship between doses and antimicrobial activities of peptides (A7, (e) and (f)) produced in Example 1 on various gram-negative bacteria.
Figure 8:
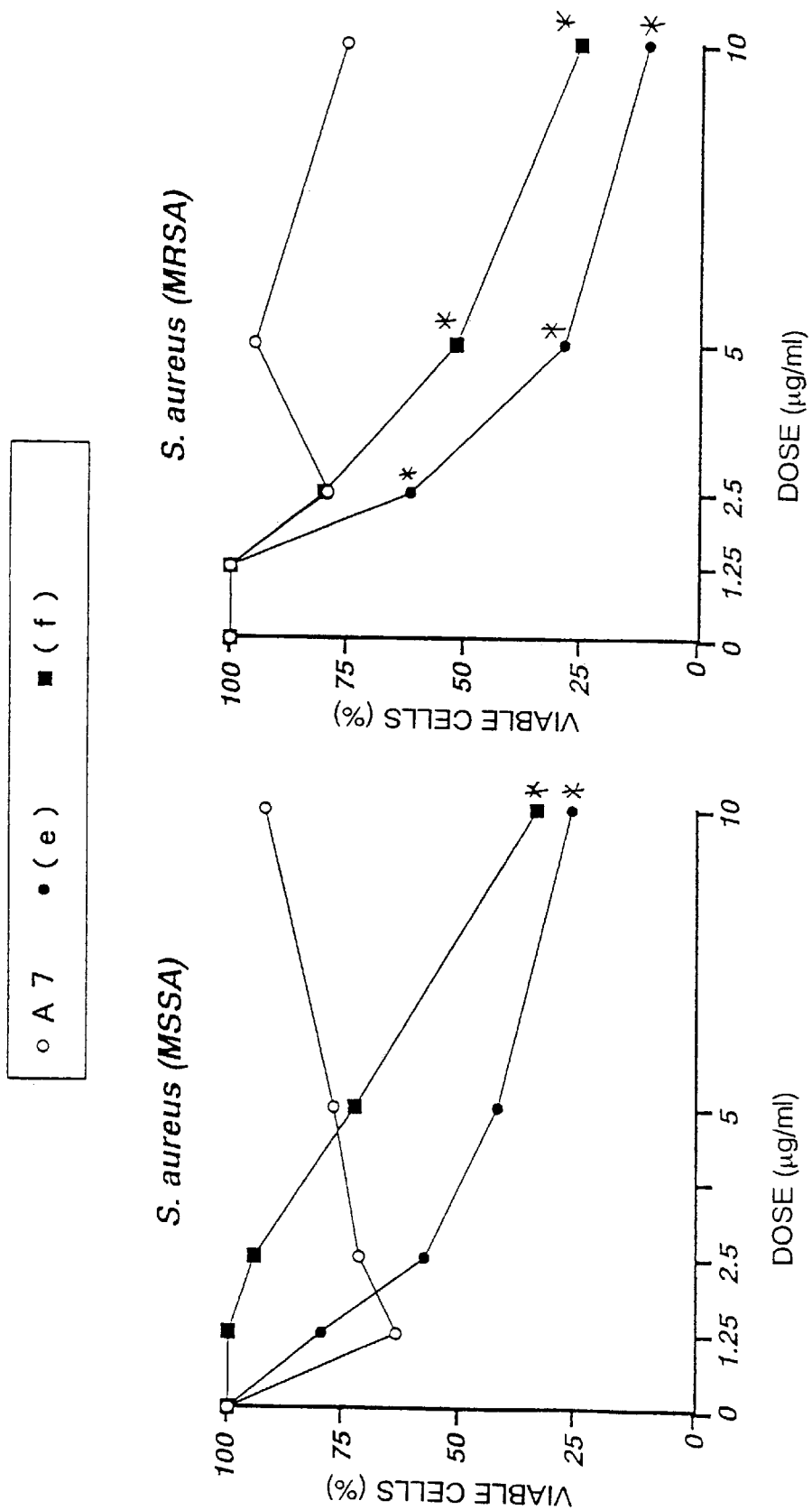
FIG. 8 shows relationship between doses and antimicrobial activities of peptides (A7, (e) and (f)) produced in Example 1 on various gram-positive bacteria.

Also, various concentrations of A7, the peptide of the present invention (e) or the peptide of the present invention (f) were used as samples and the colony-forming unit (CFU) was counted. FIG. 7 shows the results on gram-negative bacteria and FIG. 8 shows the results on gram-positive bacteria. In FIGS. 7 and 8, the horizontal axis indicates concentration of a sample and the vertical axis indicates a relative value of CFU obtained taking CFU when PBS (concentration of sample: 0 µg/ml) was used instead of a sample (peptide) as 100%. Also, in FIGS. 7 and 8, the symbol * means a significant difference at p<0.05 for the results obtained using PBS (concentration of sample: 0 µg/ml) instead of a sample (peptide).

FIGS. 7 and 8 show that the antimicrobial activity of the peptide of the present invention (substituted form) is dose-dependent and the peptide of the present invention has a higher antimicrobial activity than the unsubstituted form (known).

Based on the results shown in FIGS. 7 and 8, the antimicrobial activity ($IC_{50}$) of samples (A7, the peptide of the present invention (e) or the peptide of the present invention (f)) was obtained. The results are shown in Table 8.

TABLE 8

| Sample | Antimicrobial Activity ($IC_{50}$); µg/mL | | | |
| --- | --- | --- | --- | --- |
|  | E. coli | S. typhi. | MSSA | MRSA |
| A7 (unsubstituted form) | >20 | >20 | >20 | >20 |
| Peptide of the present invention (e) (substituted form) | 2.6 | 3.0 | 3.6 | 3.2 |
| Peptide of the present invention (f) (substituted form) | 0.8 | 1.6 | 6.6 | 5.4 |

Table 8 reveals that that the peptide of the present invention (substituted form) had an antimicrobial activity by at least about 3 to 25 folds higher than the unsubstituted form (known) on both gram-negative and gram-positive bacteria.

3-2. LPS-Neutralizing Activity (Lethality-Suppressing Activity)

Method for measuring LPS-neutralizing activity: For each mouse, 20 µg or 40 µg of a sample (peptide), 0.1 µg of LPS and 25 mg of galactosamine were injected intraperitoneally. The survival of mice was observed (for 30 days) and a survival ratio (%) was obtained.

3-2-1. LPS-Neutralizing Activity (1)

Using A1, the peptide of the present invention (b), A3 and the peptide of the present invention (d) as samples, LPS-neutralizing activities were examined by the above-described measurement method. The results are shown in Table 9. The number of mice used is also shown in Table 9.

TABLE 9

| Sample | Dose of Sample (µg/ mouse) | Number of mice (death/ total) | Survival ratio (%) |
| --- | --- | --- | --- |
| PBS 27-mer | 0 | 24/27 | 11.1 |
| A1 (unsubstituted form) | 40 | 7/8 | 12.5 |
| Peptide of the present | 40 | 0/17 | 100.0* |

TABLE 9-continued

| Sample | Dose of Sample (µg/ mouse) | Number of mice (death/ total) | Survival ratio (%) |
| --- | --- | --- | --- |
| invention (b) (substituted form) 22-mer | 20 | 1/8 | 87.5* |
| A3 (unsubstituted form) | 40 | 8/8 | 0.0 |
| Peptide of the present invention (d) (substituted form) | 40 | 2/16 | 87.5* |
|  | 20 | 4/8 | 50.0 |

Table 9 reveals that that the peptide of the present invention (substituted form) had an LPS-neutralizing activity by about 8 folds or more than the unsubstituted form (known) and suppressed lethality due to LPS.

3-2-2. LPS-Neutralizing Activity (2)

Using A1, the peptide of the present invention (b), the peptide of the present invention (a) and the peptide of the present invention (c) as samples, LPS-neutralizing activities were examined by the above-described measurement method. The results are shown in Table 10. The number of mice used is also shown in Table 10.

TABLE 10

| Sample | Dose of Sample (µg/ mouse) | Number of mice (death/ total) | Survival ratio (%) |
| --- | --- | --- | --- |
| PBS 27-mer | 0 | 33/39 | 15.4 |
| A1 (unsubstituted form) | 40 | 7/8 | 12.5 |
| Peptide of the present invention (b) (substituted form) | 20 | 2/17 | 83.0* |
|  | 40 | 1/25 | 96.0* |
| Peptide of the present invention (a) (substituted form) | 20 | 6/9 | 33.3 |
|  | 40 | 4/8 | 50.0 |
| Peptide of the present invention (c) (substituted form) | 20 | 0/9 | 100.0* |
|  | 40 | 0/8 | 100.0* |

In table above, the symbol * indicates that a significant difference at p < 0.01 ($\chi^2$ test) for the results on the case where LPS and galactosamine alone were administered.

Table 10 reveals that that the peptide of the present invention (substituted form) had an LPS-neutralizing activity by about 4 to 8 folds higher than the unsubstituted form (known) and suppressed lethality due to LPS.

In the above-described LPS-neutralizing activity tests (1) and (2), no symptom was observed in mice other than was usually observed when LPS was administrated. Therefore, it is considered that the peptide of the present invention shows no acute toxicity.

3-2-3. LPS-Neutralizing Activity of Modified Peptide

Using peptides having acetylated N-terminal and amidated C-terminal thereof (A7, the peptide of the present invention (e), and the peptide of the present invention (f)) as samples, LPS-neutralizing activities were examined by the above-described measurement method. The results are shown in Table 11. The number of mice used is also shown in Table 11.

TABLE 11

| Sample | Dose of Sample (μg/ mouse) | Number of mice (death/ total) | Survival ratio (%) |
| --- | --- | --- | --- |
| PBS | 0 | 13/13 | 0.0 |
| 18-mer | | | |
| A7 (unsubstituted form) | 40 | 7/10 | 30.0 |
| Peptide of the present invention (e) (substituted form) | 20 | 8/10 | 20.0 |
| Peptide of the present invention (f) (substituted form) | 20 | 0/10 | 100.0* |
|  | 40 | 3/10 | 70.0* |

In the table above, the symbol * indicates that a significant difference at p < 0.01 ($\chi^2$ test) for the results on the case where LPS and galactosamine alone were administered.

Table 11 reveals that that the modified peptide of the present invention (substituted form) (f) had an LPS-neutralizing activity by about 2 to 3 folds higher than the modified unsubstituted form (known) and suppressed lethality due to LPS. The activity was not influenced by the modification of peptide.

<4> Endotoxin Removal Test

An endotoxin-free carrier (Sepharose 4B (manufactured by Pharmacia)) (100 ml) was transferred to a glass filter (#2) and washed with 2 liters of distilled water for injection under suction and then charged in a 1-liter beaker, and 200 ml of distilled water for injection was added to the beaker. While stirring with a magnetic stirrer, the mixture was adjusted to pH 11 to 12 with 10 M NaOH and a solution of 25 g of cyanogen bromide (CNBr) in 500 ml of distilled water for injection was added portionwise until no change in pH occurred and then the reaction was stopped. The CNBr-activated carrier was filtered through glass filter and serially washed with 2 liters of cold water and 1 liter of 0.1 M NaHCO$_3$. To 10 ml of the obtained CNBr-activated carrier, a lyophilized preparation of the peptide of the present invention (b) was added to make 0.2 mg/ml and the mixture was treated at 4° C. for 24 hours while stirring with a rotator. After the reaction was completed, the reaction mixture was left to stand in 0.2 M tris-HCl buffer (pH 8.0) for 5 hours in order to deactivate the remaining impurities (imidocarbonate).

To 1.0 g of the thus-obtained peptide of the present invention-immobilized carrier (carrier to which the peptide of the present invention was immobilized), 5 ml of endotoxin-containing solution (0.1, 1.0, 10 or 100 ng/ml) was added and treated by continuously stirring for 30 minutes using a multi-shaker. After the treatment, the peptide of the present invention-immobilized carrier was sedimented by centrifugation and the supernatant was recovered. To 50 μl of the supernatant, 50 μl of an endotoxin-specific synthetic substrate reagent (Endospecy ES-50M, manufactured by Seikagaku Corp.) was added and the concentration of endotoxin in the solution was measured. A value of "(concentration of endotoxin before treatment−concentration of endotoxin after treatment)/concentration of endotoxin before treatment×100" was calculated and defined as an endotoxin removal ratio (%). The results are shown in Table 12.

TABLE 12

| Concentration of Endotoxin in Supernatant | | Endotoxin Removal Rate |
| --- | --- | --- |
| Before treatment | After treatment | (%) |
| 0.1 | 0 | 100 |
| 1 | 0 | 100 |
| 10 | 0 | 100 |
| 100 | 0.4 | 99.6 |

Table 12 reveals that treatment of the endotoxin-containing solution with the peptide of the present invention-immobilized carrier removed the endotoxin in the solution very well.

Example 2

Hereafter, formulation examples of the antimicrobial medicine of the present invention, the bacterial infection-treating agent of the present invention, and the endotoxin shock suppressant of the present invention will be described. However, these are merely examples and the form of the respective agents of the present invention should not be construed as being limited thereto.

(1) Antimicrobial Medicine of the Present Invention (Ointment)

| | |
| --- | --- |
| Peptide of the present invention (d) | 10 mg |
| Sorbitan monostearate | 7 mg |
| Polyoxyethylene sorbitan monostearate | 7 mg |
| Isopropyl palmitate | 37 mg |
| Vaseline | 37 mg |
| Liquid paraffin | 37 mg |
| Cetanol | 50 mg |
| Glycerol | 70 mg |
| Magnesium stearate | 2 mg |

Purified water was added to the above-described components to make 1 g of cream.

(2) Antimicrobial Medicine of the Present Invention (Tablet)

| | |
| --- | --- |
| Peptide of the present invention (c) | 100 mg |
| Lactose | 670 mg |
| Potato starch | 150 mg |
| Crystalline cellulose | 60 mg |
| Light silicic anhydride | 50 mg |

The above-described components were mixed and after kneading with addition of a solution of 30 mg of hydroxypropylcellulose in methanol (10% by weight of hydroxypropylcellulose), the mixture was granulated. This was extruded through a 0.8 mm-diameter screen to form granules. After drying, 15 mg of magnesium steararate was added and the mixture was tabulated in amounts of 200 mg each to obtain tablets.

(3) Bacterial Infection-Treating Agent of the Present Invention (Capsule)

| | |
| --- | --- |
| Peptide of the present invention (d) | 100 mg |
| Lactose | 80 mg |

The above-described components were mixed uniformly and filled in hard capsules to obtain capsules.

(4) Bacterial Infection-Treating Agent of the Present Invention (Injection)

| | |
|---|---|
| Peptide of the present invention (e) | 30 mg |

The above-described component was dissolved in 2 ml of 5% aqueous mannitol solution and the solution was filter-sterilized and then charged in an ampule and sealed.

(5) Endotoxin Shock Suppressant of the Present Invention (Injectable Solid to be Dissolved when Used)

(A) Peptide of the present invention (f) (lyophilized) 30 mg (sealed in an ampule)

(B) Filter-sterilized PBS 2 ml (sealed in an ampule)

A injectable solid to be dissolved when used was provided as a set of the above-described (A) and (B). Upon use, (A) is dissolved in (B).

What is claimed is:

1. An isolated peptide comprising at least the amino acid sequence of SEQ ID NO:1,
Wherein, the Xaa at amino acid 2 comprises a hydrophobic amino acid residue, the Xaa at amino acids 8, 12 and 16 comprise a hydrophilic amino acid residue, and the Xaa at amino acid 11 comprises an arbitrary amino acid residue.

2. The isolated peptide according to claim 1, wherein said amino acid sequence is selected from the group consisting of; SEQ ID NOS:2–7.

3. An antimicrobial composition comprising the peptide as defined in claim 1 and a carrier.

4. An antimicrobial composition comprising the peptide as defined in claim 2 and a carrier.

5. A medicinal composition comprising the peptide as defined in claim 1 and a pharmaceutically acceptable carrier.

6. A medicinal composition comprising the peptide as defined in claim 2 and a pharmaceutically acceptable carrier.

7. A bacterial infection-treating composition comprising the peptide as defined in claim 1 and a pharmaceutically acceptable carrier.

8. A bacterial infection-treating composition comprising the peptide as defined in claim 2 and a pharmaceutically acceptable carrier.

9. An endotoxin shock-suppressing composition comprising the peptide as defined in claim 1 and a pharmaceutcally acceptable carrier.

10. An endotoxin shock-suppressing composition comprising the peptide as defined in claim 2 and a pharmaceutically acceptable carrier.

11. An endotoxin-removing agent comprising the peptide as defined in claim 1 immobilized to an insoluble carrier.

12. An endotoxin-removing agent comprising the peptide as defined in claim 2 immobilized to an insoluble carrier.

13. A method for treating bacterial infection, comprising administering to a living body in need of such treatment a therapeutically effective amount of the peptide as defined in claim 1.

14. A method for treating endotoxin shock, comprising administering to a living body in need of such treatment a therapeutically effective amount of the peptide as defined in claim 1.

15. A method for removing an endotoxin from a solution, comprising contacting a carrier to which the peptide as defined in claim 1 is immobilized, with a solution in which removal of the endotoxin is desired, to form a complex of the endotoxin in the solution and the peptide which is immobilized to the carrier, and separating the carrier from the solution.

16. A composition comprising the peptide as defined in claim 1 and a carrier.

* * * * *

SEQUENCE LISTING

```
<160> NUMBER OF SEQ ID NOS: 12

<210> SEQ ID NO 1
<211> LENGTH: 18
<212> TYPE: PRT
<213> ORGANISM: Artificial Sequence
<220> FEATURE:
<223> OTHER INFORMATION: A human-derived peptide of CAP18 wherein Xaa at
      position 2 = a hydrophobic amino acid, Xaa at
      positions 8, 12, and 16 = a hydrophilic amino
      acid, and Xaa at position 11 - any amino acid.

<400> SEQUENCE: 1

Lys Xaa Phe Lys Arg Ile Val Xaa Arg Ile Xaa Xaa Phe Leu Arg Xaa
1               5                   10                  15

Leu Val

<210> SEQ ID NO 2
<211> LENGTH: 27
<212> TYPE: PRT
<213> ORGANISM: Artificial Sequence
<220> FEATURE:
<223> OTHER INFORMATION: A human-derived peptide of CAP18 with
      substitutions.

<400> SEQUENCE: 2

Phe Arg Lys Ser Lys Glu Lys Ile Gly Lys Leu Phe Lys Arg Ile Val
1               5                   10                  15

Gln Arg Ile Lys Asp Phe Leu Arg Asn Leu Val
            20                  25

<210> SEQ ID NO 3
<211> LENGTH: 27
<212> TYPE: PRT
<213> ORGANISM: Artificial Sequence
<220> FEATURE:
<223> OTHER INFORMATION: A human-derived peptide of CAP18 with
      substitutions.

<400> SEQUENCE: 3

Phe Arg Lys Ser Lys Glu Lys Ile Gly Lys Leu Phe Lys Arg Ile Val
1               5                   10                  15

Gln Arg Ile Leu Asp Phe Leu Arg Asn Leu Val
            20                  25

<210> SEQ ID NO 4
<211> LENGTH: 27
<212> TYPE: PRT
<213> ORGANISM: Artificial Sequence
<220> FEATURE:
<223> OTHER INFORMATION: A human-derived peptide of CAP18 with
      substitutions.
```

```
<400> SEQUENCE: 4

Phe Arg Lys Ser Lys Glu Lys Ile Gly Lys Phe Phe Lys Arg Ile Val
1               5                   10                  15

Gln Arg Ile Phe Asp Phe Leu Arg Asn Leu Val
            20                  25

<210> SEQ ID NO 5
<211> LENGTH: 22
<212> TYPE: PRT
<213> ORGANISM: Artificial Sequence
<220> FEATURE:
<223> OTHER INFORMATION: A human-derived peptide of CAP18 with
      substitutions.

<400> SEQUENCE: 5

Glu Lys Ile Gly Lys Leu Phe Lys Arg Ile Val Gln Arg Ile Leu Asp
1               5                   10                  15

Phe Leu Arg Asn Leu Val
            20

<210> SEQ ID NO 6
<211> LENGTH: 18
<212> TYPE: PRT
<213> ORGANISM: Artificial Sequence
<220> FEATURE:
<223> OTHER INFORMATION: A human-derived peptide of CAP18 with
      substitutions.

<400> SEQUENCE: 6

Lys Leu Phe Lys Arg Ile Val Gln Arg Ile Leu Asp Phe Leu Arg Asn
1               5                   10                  15

Leu Val

<210> SEQ ID NO 7
<211> LENGTH: 18
<212> TYPE: PRT
<213> ORGANISM: Artificial Sequence
<220> FEATURE:
<223> OTHER INFORMATION: A human-derived peptide of CAP18 with
      substitutions.

<400> SEQUENCE: 7

Lys Leu Phe Lys Arg Ile Val Lys Arg Ile Leu Lys Phe Leu Arg Lys
1               5                   10                  15

Leu Val

<210> SEQ ID NO 8
<211> LENGTH: 27
<212> TYPE: PRT
<213> ORGANISM: Artificial Sequence
<220> FEATURE:
<223> OTHER INFORMATION: A human-derived peptide of CAP18 with
      substitutions.

<400> SEQUENCE: 8

Phe Arg Lys Ser Lys Glu Lys Ile Gly Lys Glu Phe Lys Arg Ile Val
1               5                   10                  15

Gln Arg Ile Lys Asp Phe Leu Arg Asn Leu Val
            20                  25

<210> SEQ ID NO 9
<211> LENGTH: 22
<212> TYPE: PRT
```

-continued

```
<213> ORGANISM: Artificial Sequence
<220> FEATURE:
<223> OTHER INFORMATION: A human-derived peptide of CAP18 with
      substitutions.

<400> SEQUENCE: 9

Glu Lys Ile Gly Lys Glu Phe Lys Arg Ile Val Gln Arg Ile Lys Asp
 1               5                  10                  15

Phe Leu Arg Asn Leu Val
            20

<210> SEQ ID NO 10
<211> LENGTH: 24
<212> TYPE: PRT
<213> ORGANISM: Artificial Sequence
<220> FEATURE:
<223> OTHER INFORMATION: A human-derived peptide of CAP18 with
      substitutions.

<400> SEQUENCE: 10

Ser Lys Glu Lys Ile Gly Lys Glu Phe Lys Arg Ile Val Gln Arg Ile
 1               5                  10                  15

Lys Asp Phe Leu Arg Asn Leu Val
            20

<210> SEQ ID NO 11
<211> LENGTH: 23
<212> TYPE: PRT
<213> ORGANISM: Artificial Sequence
<220> FEATURE:
<223> OTHER INFORMATION: A human-derived peptide of CAP18 with
      substitutions.

<400> SEQUENCE: 11

Lys Glu Lys Ile Gly Lys Glu Phe Lys Arg Ile Val Gln Arg Ile Lys
 1               5                  10                  15

Asp Phe Leu Arg Asn Leu Val
            20

<210> SEQ ID NO 12
<211> LENGTH: 18
<212> TYPE: PRT
<213> ORGANISM: Artificial Sequence
<220> FEATURE:
<223> OTHER INFORMATION: A human-derived peptide of CAP18 with
      substitutions.

<400> SEQUENCE: 12

Lys Glu Phe Lys Arg Ile Val Gln Arg Ile Lys Asp Phe Leu Arg Asn
 1               5                  10                  15

Leu Val
```